United States Patent
Kuban et al.

(10) Patent No.: US 8,460,214 B2
(45) Date of Patent: Jun. 11, 2013

(54) VASCULAR GUIDEWIRE SYSTEM AND METHOD

(75) Inventors: Barry D. Kuban, Avon Lake, OH (US); David R. Whittaker, Potomac, MD (US); Ryan S. Klatte, Cleveland, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 730 days.

(21) Appl. No.: 12/579,267

(22) Filed: Oct. 14, 2009

(65) Prior Publication Data

US 2010/0174233 A1 Jul. 8, 2010

Related U.S. Application Data

(60) Provisional application No. 61/105,192, filed on Oct. 14, 2008.

(51) Int. Cl.
*A61M 25/09* (2006.01)
*A61M 25/092* (2006.01)

(52) U.S. Cl.
USPC ............ 600/585; 600/433; 600/434; 604/171; 604/533; 604/535

(58) Field of Classification Search
USPC ................. 600/433, 434, 585; 604/171, 528, 604/533, 535
See application file for complete search history.

(56) References Cited

U.S. PATENT DOCUMENTS

| | | | |
|---|---|---|---|
| 4,798,598 A | 1/1989 | Bonello et al. | |
| 5,090,956 A | 2/1992 | McCoy | |
| 5,353,798 A * | 10/1994 | Sieben | 600/462 |
| 5,524,635 A | 6/1996 | Uflacker et al. | |
| 5,882,333 A | 3/1999 | Schaer et al. | |
| 5,957,941 A | 9/1999 | Ream | |
| 6,231,563 B1 | 5/2001 | White et al. | |
| 6,802,809 B2 | 10/2004 | Okada | |
| 6,814,727 B2 | 11/2004 | Mansouri-Ruiz | |
| 7,128,718 B2 | 10/2006 | Hojeibane et al. | |
| 7,613,493 B2 * | 11/2009 | Mansouri-Ruiz | 600/407 |
| 2003/0088187 A1 | 5/2003 | Saadat et al. | |

(Continued)

FOREIGN PATENT DOCUMENTS

| | | |
|---|---|---|
| EP | 0 247 371 A1 | 12/1987 |
| EP | 1 358 903 A2 | 11/2003 |
| WO | WO-2006/058223 A2 | 6/2006 |
| WO | WO-2008/049088 A2 | 4/2008 |

*Primary Examiner* — Sean Dougherty
(74) *Attorney, Agent, or Firm* — Tarolli, Sundheim, Covell & Tummino LLP

(57) ABSTRACT

A vascular guidewire system includes a tubular member which at least partially encloses a core wire. A first or distal gripper is connected with a handle to grip a proximal end portion of the tubular member. A second or proximal gripper is disposed in the handle and grips a proximal end portion of the core wire. A first or distal motor is disposed in the handle and is operable to rotate the core wire relative to the outer tubular member. A second or proximal motor is disposed in the handle and is operable to move the first or distal motor longitudinally relative to the handle to thereby move the core wire longitudinally relative to the outer tubular member. The second or proximal motor is disposed in a coaxial relationship with the first or distal motor. Rotational and/or longitudinally directed forces may be manually applied to the handle to move the tubular member and core wire relative to a patient's body.

23 Claims, 9 Drawing Sheets

U.S. PATENT DOCUMENTS

| | | |
|---|---|---|
| 2004/0054322 A1* | 3/2004 | Vargas ........................ 604/95.04 |
| 2004/0116849 A1 | 6/2004 | Gardeski |
| 2005/0240116 A1* | 10/2005 | Saadat et al. .................. 600/549 |
| 2005/0273020 A1 | 12/2005 | Whittaker et al. |
| 2005/0277851 A1 | 12/2005 | Whittaker et al. |
| 2005/0277988 A1 | 12/2005 | Whittaker et al. |
| 2006/0025705 A1 | 2/2006 | Whittaker et al. |
| 2007/0179472 A1 | 8/2007 | Whittaker et al. |
| 2009/0062602 A1* | 3/2009 | Rosenberg et al. ........... 600/101 |

* cited by examiner

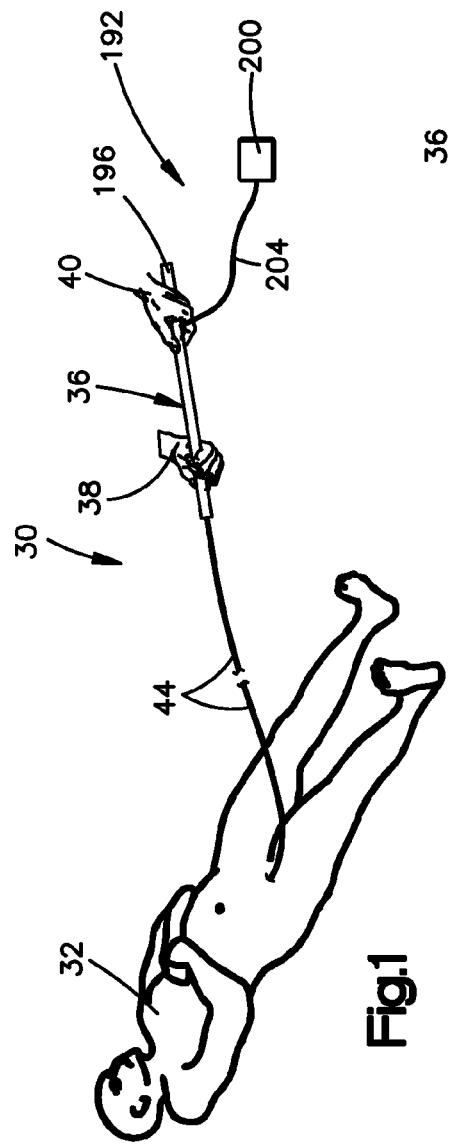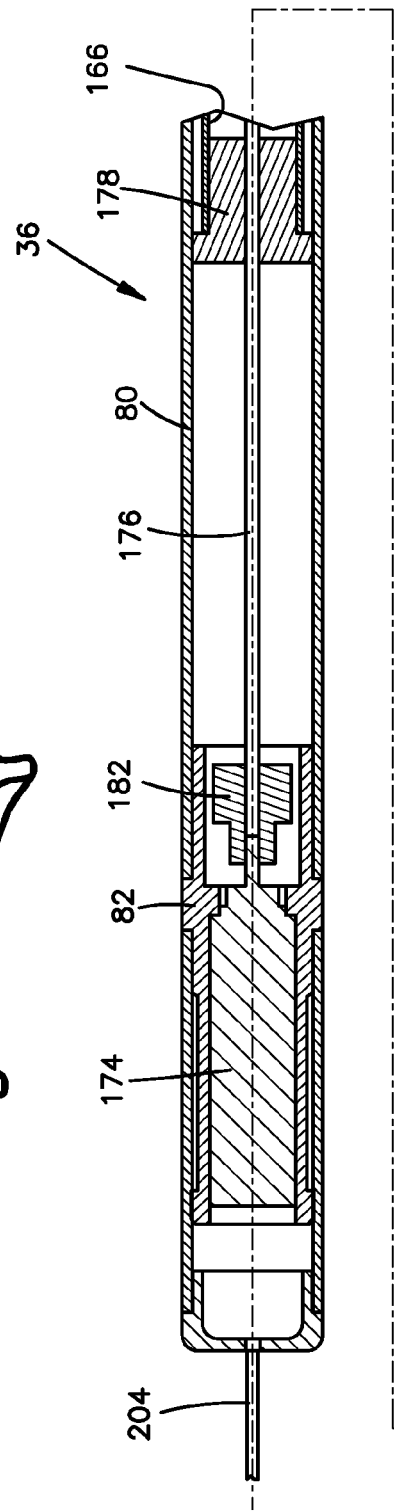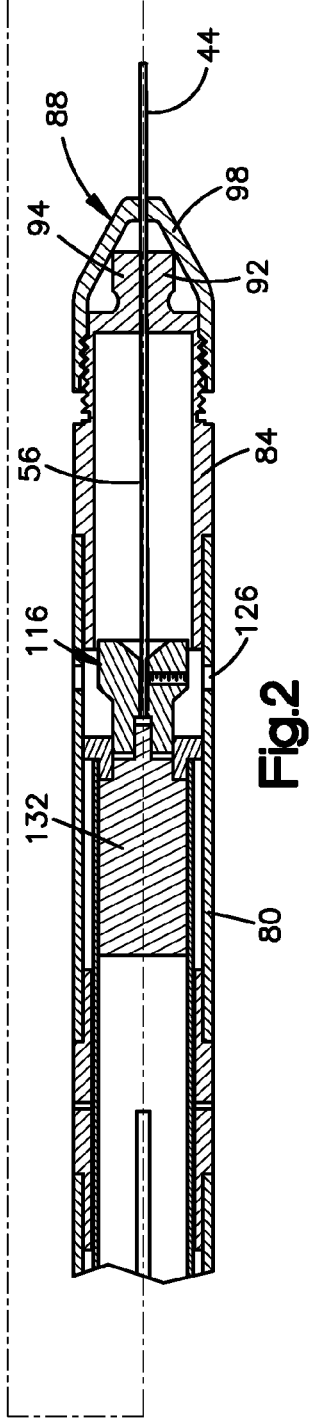

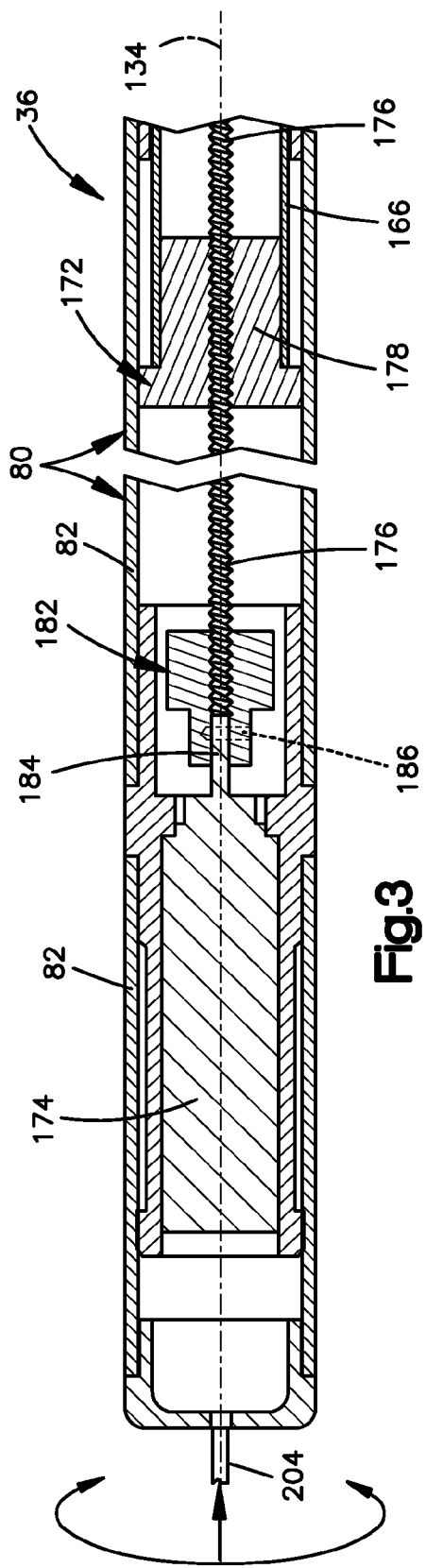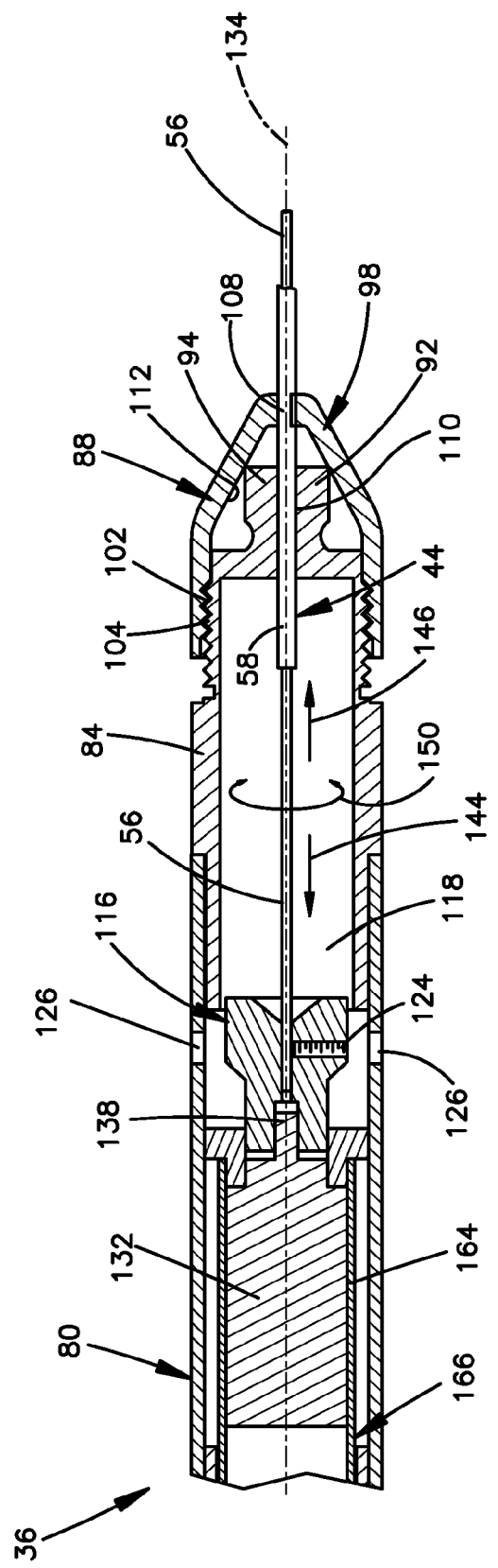

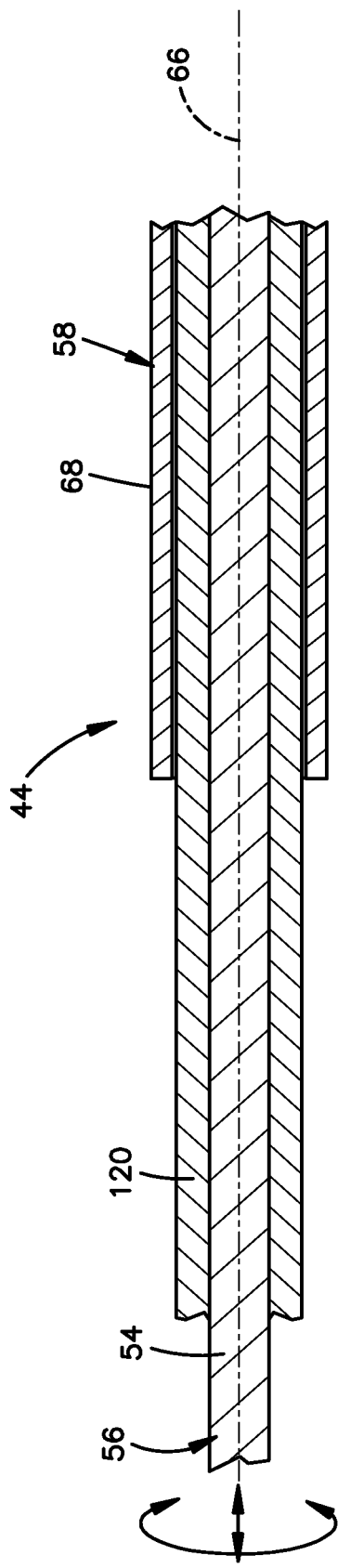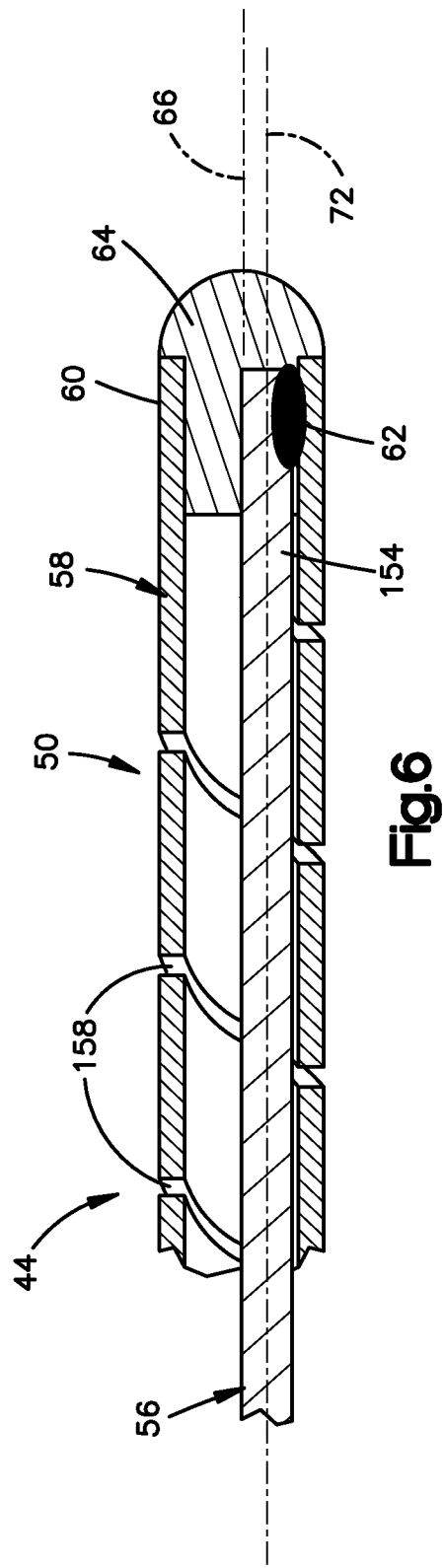

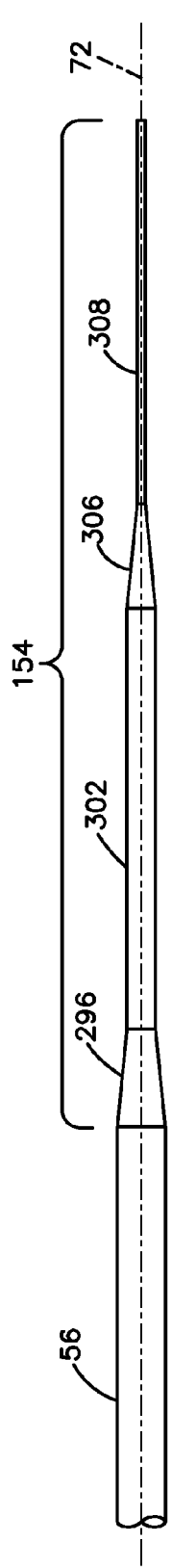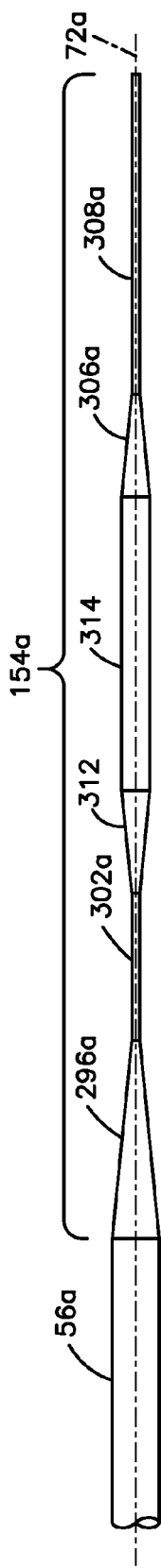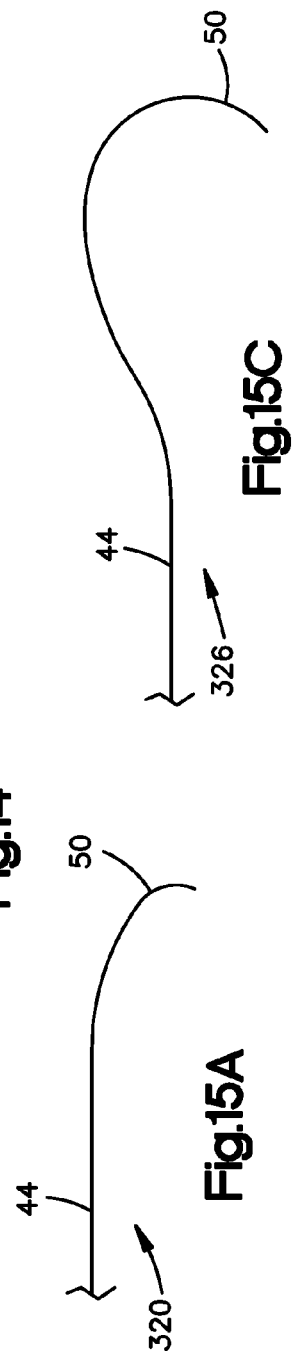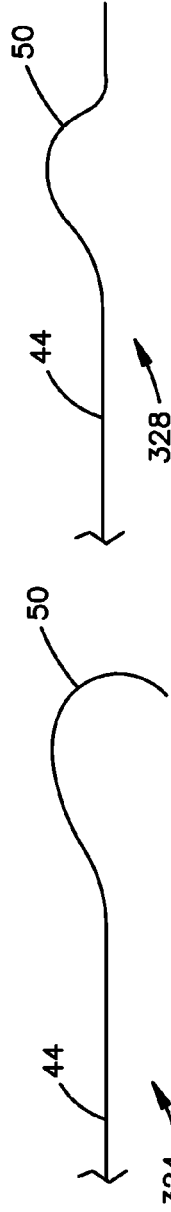

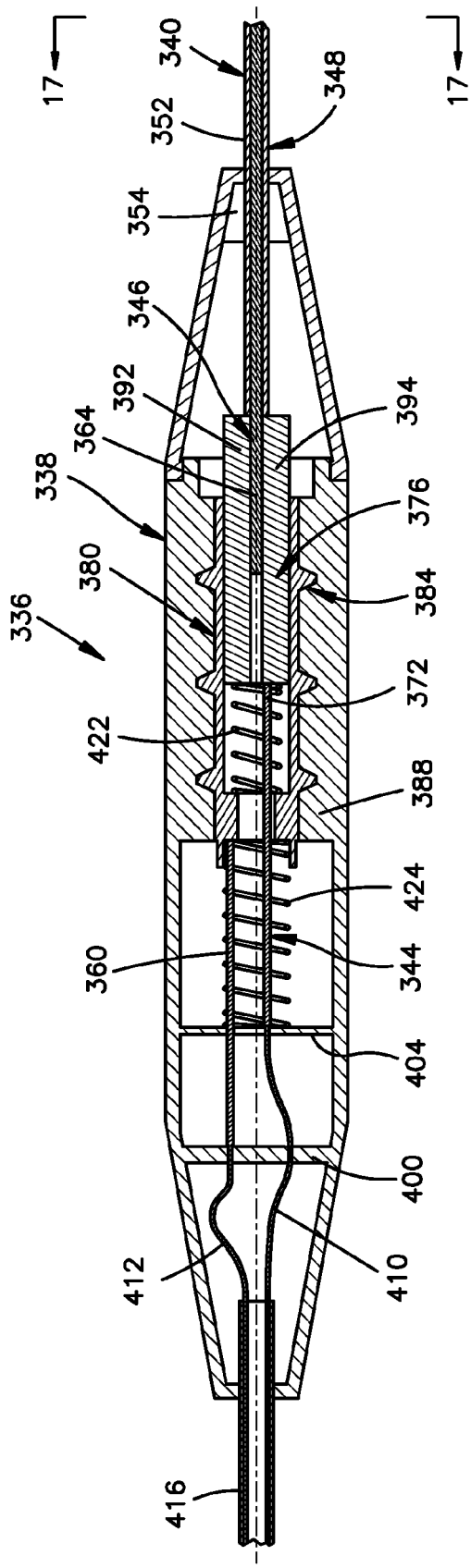
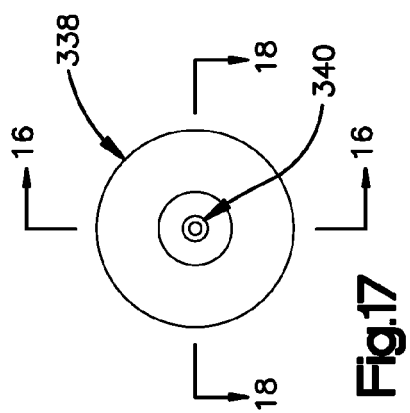
Fig.16
Fig.17

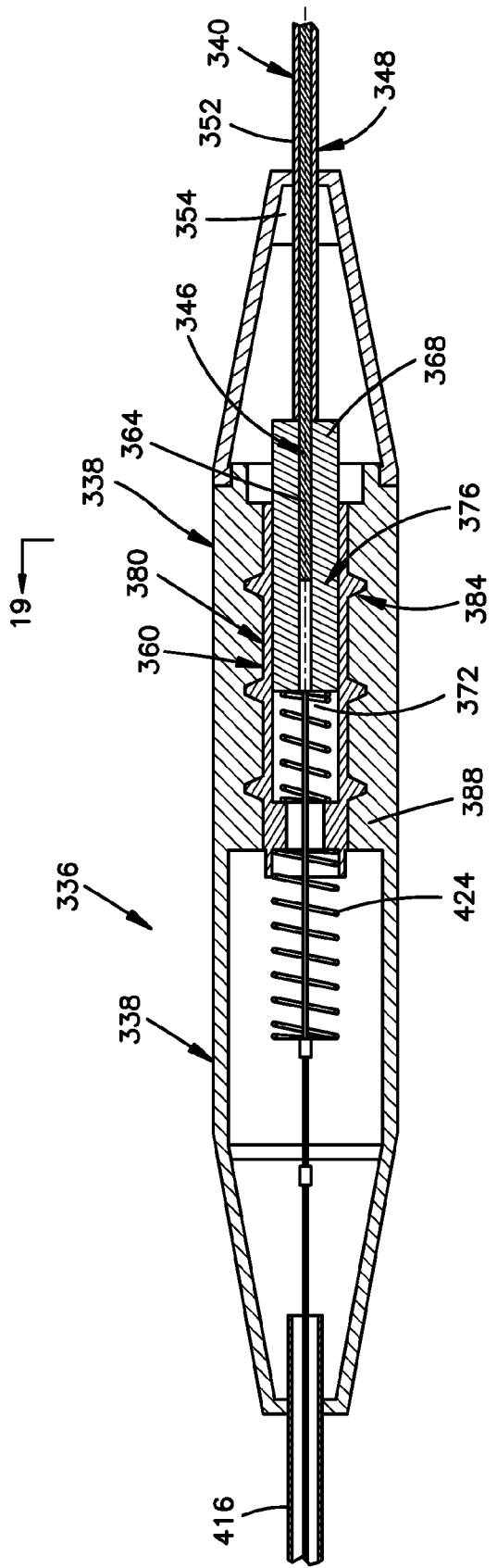
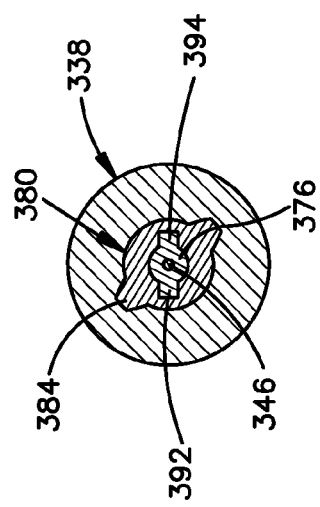
Fig.18
Fig.19

VASCULAR GUIDEWIRE SYSTEM AND METHOD

RELATED APPLICATION

This application hereby claims the benefit of the earlier filing date of U.S. Provisional Patent Application Ser. No. 61/105,192 filed Oct. 14, 2008 and entitled Variable Control Guidewire System II. The disclosure in the aforementioned Provisional Patent Application Ser. No. 61/105,192 is hereby incorporated herein in its entirety by this reference thereto.

BACKGROUND OF THE INVENTION

The present invention relates to a vascular guidewire system and a method of using the guidewire system in a patient's body.

A guidewire system may be utilized during the performance of a number of procedures including angioplasty, angiography, balloon, septostony, and electrophysiology studies. The guidewire system may be utilized in association with procedures performed on many different portions of a patient's body, such as a heart, brain, or other part of a patient's body. Known devices for use in interventional and diagnostic access, manipulation within, and negotiation of a vascular system are disclosed in United States Published Patent Application Nos. 2005/0273020; 2005/0277851; 2005/0277988; 2006/0025705; and 2007/0179472.

SUMMARY OF THE INVENTION

An improved vascular guidewire system includes a handle or housing which is connected with a tubular member or sheath. The tubular member at least partially encloses a core wire. Forces are manually applied to the handle to rotate and/or move the guidewire along a blood vessel in a vascular system.

The configuration of a distal end portion of the tubular member or sheath of the guidewire is changed by operating first and/or second motors in the handle. The first motor may be operated to rotate the core wire relative to the tubular member or sheath. The second motor may be operated to move the core wire longitudinally relative to the tubular member or sheath. The motors in the handle may advantageously be disposed in a coaxial relationship.

The present invention has a plurality of features which may be utilized together in the manner disclosed herein. Alternatively, the various features of the invention may be used in different in combinations with each other and/or features from the prior art.

BRIEF DESCRIPTION OF THE DRAWINGS

The foregoing and other features of the invention will become more apparent upon a consideration of the following description taken in connection with the accompanying drawings wherein:

FIG. 1 is a schematic illustration depicting the manner in which a vascular guidewire system constructed in accordance with the present invention is utilized in association with a patient;

FIG. 2 is a fragmentary sectional illustration of a handle or connector which is used in the vascular guidewire system of FIG. 1;

FIG. 3 is an enlarged fragmentary schematic illustration of a proximal or trailing end portion of the handle of FIG. 2;

FIG. 4 is an enlarged schematic illustration of a distal or leading end portion of the handle of FIG. 2;

FIG. 5 is an enlarged fragmentary schematic illustration of a proximal or trailing end portion of a guidewire used in the vascular guidewire system of FIG. 1 and illustrating the relationship between a tubular outer member or sheath and a core wire;

FIG. 6 is an enlarged fragmentary schematic illustration of a distal or leading end portion of the guidewire and illustrating the relationship between the tubular outer member or sheath and the core wire;

FIG. 13 is a fragmentary schematic illustration of a tapered distal end portion of the core wire of FIGS. 5 and 6;

FIG. 14 is a schematic illustration, similar to FIG. 13, of a distal end portion of a second embodiment of the core wire;

FIGS. 15A through 15D are schematic illustrations depicting various configurations which can be imparted to the distal end portion of a guidewire by operating one or more motors in the handle or connector of FIGS. 2-4;

FIG. 16 is a fragmentary schematic sectional view, taken generally along the line 16-16 of FIG. 17 illustrating the construction of a second embodiment of the handle or connector of FIGS. 2-4 and which may be utilized in the vascular guidewire system of FIG. 1;

FIG. 17 is an end view, taken generally along the line 17-17 of FIG. 16, further illustrating the construction of the handle or connector;

FIG. 18 is a fragmentary sectional view, generally similar to FIG. 16, taken along the line 18-18 of FIG. 17, and further illustrating the construction of the handle or connector of FIGS. 16 and 17; and FIG. 19 is a schematic sectional view, taken generally along the line 19-19 of FIG. 18.

DESCRIPTION OF SPECIFIC PREFERRED EMBODIMENTS OF THE INVENTION

General Description

Figure 7:
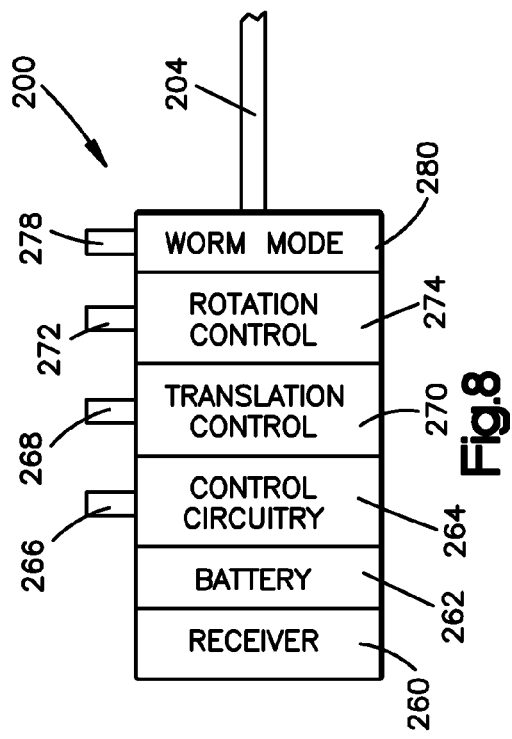
FIG. 7 is a schematic illustration of a hand held switch assembly which forms part of a control apparatus used in the vascular guidewire system of FIG. 1.

A vascular guidewire system 30 constructed in accordance with the present invention is illustrated schematically in FIG. 1 in association with a patient 32. The vascular guidewire system 30 includes a handle or connector 36 which is gripped by the hands 38 and 40 of a person using the vascular guidewire system. A guidewire 44 extends from the handle or connector 36 and is received in a blood vessel in the body of the patient 32. Force which is manually applied to the handle or connector 36 rotates moves and the guidewire 44 longitudinally relative to the patient during performance of the illustrated cardiac catherization procedure. The handle or connector 36 is as small, light and unobtrusive as possible so as not to interfere with normal manipulation of the guidewire 44. Of course, the vascular guidewire system 30 may be utilized during the performance of any one of many known procedures.

In order to facilitate movement of the guidewire along a desired path in a patient's vascular system, the configuration of a distal or leading end portion 50 (FIG. 6) of the guidewire 44 can be changed as a function of the configuration of various portions of the path along which it is desired to move the guidewire. To change the configuration of the distal or leading end portion 50 (FIG. 6) of the guidewire 44, a proximal or trailing end portion 54 (FIG. 5) of a core wire 56 is rotated and/or moved longitudinally relative to a tubular outer member or sheath 58.

The distal or leading end portion 50 of the core wire 56 is fixedly connected to a distal or a leading end portion 60 (FIG. 6) of the outer tubular member 58 at a connection 62. The connection 62 is offset to one side of a longitudinal central axis 66 of the outer tubular member or sheath 58. A plug 64 is advantageously provided in the distal end portion 60 of the outer tubular member or sheath 58. However, the plug 64 may be omitted if desired. A plug 64 is advantageously provided in the distal end portion 60 of the outer tubular member or sheath 58. However, the plug 64 may be omitted if desired.

At the proximal or trailing end portion 68 (FIG. 5) of the tubular member or sheath 58, the central axis of the core wire 56 is coincident with the central axis 66 of the outer tubular member or sheath 58. At the distal or leading end portion 60 of the tubular member or sheath 58, the longitudinal central axis 72 (FIG. 6) of the core wire 56 is offset from the longitudinal central axis 66 of the outer tubular member or sheath 58. However, if desired, the central axis 72 of the core wire 56 may be coincident with the central axis 66 of the outer tubular member or sheath 58 at the distal end portion 60 of the outer tubular member.

Handle or Connector

The handle or connector 36 (FIGS. 2-4) is constructed and used in accordance with one of the features of the present invention. The handle or connector 36 includes a generally cylindrical housing 80. The housing 80 has a proximal or trailing end portion 82 (FIG. 3) and a distal or leading end portion 84 (FIG. 4).

A distal or leading gripper 88 (FIG. 4) is disposed at the distal end portion 84 of the housing 80. The distal or leading gripper 88 grips the proximal or trailing end portion 68 (FIG. 5) of the outer tubular metal member or sheath 58 to hold the proximal end portion 68 of the outer tubular metal member stationary relative to the housing 80. The distal or leading gripper 88 includes a plurality of jaws 92 and 94. Although a pair of jaws have been illustrated schematically in FIG. 4, it should be understood that a greater number of jaws may be provided if desired. For example, the distal or leading gripper 88 may include three jaws which are evenly spaced around the proximal or trailing end portion 68 (FIG. 5) of the outer tubular member or sheath 58.

An end cap 98 (FIG. 4) has an internal thread 102 which engages an external thread 104 on the housing 80. A proximal end portion of the guidewire 44 extends through a circular opening 108 in the end cap 98 into a passage 110 formed by the jaws 92 and 94. The outer tubular member or sheath 58 extends a short distance past the end of the passage 110. The metal core wire 56 (FIG. 5) extends outwardly past the proximal end of the tubular member or sheath 58.

When the end cap 98 (FIG. 4) is rotated relative to the housing 80, a cam surface 112 on the inside of the end cap 98 is pressed against the jaws 92 and 94. The force applied against the jaws 92 and 94 by the end cap 98 resiliently deflects the jaws to firmly grip the proximal end portion 68 of the tubular member or sheath 58. This results in the tubular metal member or sheath 58 being held against both rotational and longitudinal movement relative to the housing 80 by the distal or leading gripper 88. However, the proximal or trailing end portion 54 (FIG. 5) of the metal core wire 56 is rotatable and movable longitudinally relative to both the outer tubular member or sheath 58 and the housing 80.

The proximal or trailing end portion 54 of the core wire 56 (FIG. 5) is gripped by a second gripper 116 (FIG. 4) disposed in a cylindrical chamber 118 in the housing 80. In the illustrated embodiment of the guidewire 44, an intermediate tubular member 120 (FIG. 5) extends around and is fixedly connected to the proximal or trailing end portion 54 of the core wire 56. The intermediate tubular member forms part of the core wire 56 and is effective to increase the diameter of the proximal end portion 54 of the core wire 56. This facilitates gripping of the proximal or trailing end portion 54 of the core wire with the gripper 116.

Although the intermediate tubular member 120 has been illustrated in FIG. 5 as ending before the proximal end of the core wire 56, the intermediate tubular member 120 extends to the proximal end of the core wire 56. Therefore, annular proximal end surface of the intermediate tubular member 120 and a circular proximal end surface of the core wire 56 are disposed in the same plane. This results in both the intermediate tubular member 120 (FIG. 5) and the core wire 56 extending into the second gripper 116 (FIG. 4).

A set screw 124 in the second gripper 116 is accessible through openings 126 in the housing 80. The intermediate tubular member 120 is fixedly connected to the core wire 56 and is engaged by the set screw 124 to clamp both the intermediate tubular member 120 and the core wire 56 against movement relative to the second gripper 116. The intermediate tubular member 120 extends through the distal or leading gripper 88 and the opening 108 in the end cap 98. A short distance distally, that is toward the right as viewed in FIG. 4, from the end cap 98, the intermediate tubular member 120 ends. If desired, the intermediate tubular member 120 may be omitted.

A first or distal motor 132 (FIG. 4) is connected to the second gripper 116 and is operable to rotate the second gripper about a central axis 134 of the handle or connector 36. The central axis 134 is coincident with the central axis 72 of the portion of the core wire 56 which is gripped by the second gripper 116. The central axis 134 of the handle or connector is also coincident with the central axis of the proximal portion of the outer tubular member or sheath 58 and core wire 56.

The first or distal motor 132 is a reversible electric motor and has an output shaft 138 which is fixedly connected to the second gripper 116. The central axis of the output shaft 138 is coincident with the central axis 134 of the handle or connector 36. Operation of the first or distal motor 132 is effective to rotate the second gripper 116 and the proximal or trailing end portion 54 (FIG. 5) of the core wire 56 about the central axis 134 of the handle or connector 36. However the first gripper 88 holds the outer tubular member or sheath 58 against movement relative to the handle 36.

The first or distal motor 132 (FIG. 4) is movable along the central axis 134 of the handle 36 to move the core wire 56 (FIG. 5) longitudinally relative to the outer tubular member or sheath 58. Thus, the first or distal motor 132 is movable axially in either a proximal direction, that is, toward the left as viewed in FIG. 4 and indicated by an arrow 144, or in a distal direction, that is toward the right as viewed in FIG. 4 and indicated by an arrow 146. Upon operation of the first or distal motor 132, the core wire 56 is rotatable in either one of two directions, indicated by arrows 150 in FIG. 4. As was previously mentioned, the first or distal motor 132 is a reversible electric motor.

By moving the core wire 56 (FIG. 5) relative to the tubular outer member or sheath 58, the configuration of the distal end portion 50 (FIG. 6) of the guidewire 44 is resiliently changed. Movement of the core wire 56, that is either rotational or longitudinal movement, is effective to resiliently deflect the distal or leading end portion 50 of the guidewire 44. This change in the configuration of the distal or leading end portion 50 of the guidewire 44 (FIG. 6) occurs because a distal or leading end portion 154 of the core wire 56 is fixedly connected to the distal or leading end portion 60 of the tubular member or sheath 58 at the connection 62. The fact that the central axis 72 of the core wire 56 is offset from the central axis 66 of the outer tubular member 58 at the connection 62 (FIG. 6) facilitates resilient deflection of the distal or leading end portion 50 of the guidewire 44 when the core wire 56 is moved with either rotational or longitudinal movement.

In addition, resilient deflection of the distal or leading end portion 50 of the guidewire 44 is facilitated by a helical slot 158 in the distal or leading end portion 50 of the outer tubular metal member or sheath 58. It is contemplated that the distal or leading end portion 50 of the outer tubular member 58 may be formed with openings other than a helical slot. For example, a series of slots, with each slot in the series of slots extending only partway around the outer tubular member or sheath 58, may be formed in the distal or leading end portion 50 of the tubular member. As another example, generally H-shaped slots may be formed in the distal or leading end portion 50 of the tubular member 58 with the legs of the H-shaped slots extending circumferentially partway around the outer tubular member or sheath and the central crossbar of the H-shaped slots extending axially along the outer tubular member or sheath. Of course, the distal or leading end portion 50 of the outer tubular member or sheath 58 may be formed with a continuous side wall which is free of slots if desired.

To enable the first or distal motor 132 (FIG. 4) to move axially along the housing 80 to the handle 36, the motor 132 is fixedly mounted on the distal or right (as viewed in FIG. 4) end portion 164 of a carriage 166 (FIGS. 2, 3 and 4). The carriage 166 is movable along the longitudinal central axis 134 of the handle 36. Thus, the carriage 166 is movable either proximally, as indicated by the arrow 144 in FIG. 4, or distally, as indicated by the arrow 146 in FIG. 4, relative to the housing 80.

A drive assembly 172 (FIG. 3) is connected with the carriage 166 and is operable by a second or proximal motor 174 disposed in the handle 36. The drive assembly 172 includes a screw 176 having an external thread convolution which engages an internal thread convolution on a nut 178. The nut 178 is fixedly connected to the proximal end portion of the carriage 166.

Upon operation of the motor 174, the carriage 166 is moved along the longitudinal central axis 134 of the handle 36 by interaction between the screw 176 and the nut 178. The second or proximal motor 174 is a reversible electric motor which is operable to rotate the screw 176 in either a clockwise or counterclockwise direction. The screw 176 is connected with the reversible electric motor 174 by a third gripper 182.

The gripper 182 is fixedly connected to an output shaft 184 (FIG. 3) of the second or proximal motor 174. The motor output shaft 184 is rotatable in either a clockwise or counterclockwise direction about a longitudinal central axis 134 of the handle 36. The gripper 182 is fixedly connected with the output shaft 184 by a set screw 186. The gripper 182 securely holds or grips the distal end portion of the screw 176.

Rotation of the motor output shaft 184 is effective to rotate the gripper 182 and drive screw 176 about their longitudinal central axes which are coincident with the longitudinal central axis 134 of the handle 36. Rotation of the drive screw 176 causes longitudinal movement of the carriage 166 and the first or distal motor 132 (FIG. 4) along the central axis 134 of the handle 36. Since the output shaft 138 of the motor 132 is fixedly connected to the core wire 56 by the gripper 116, longitudinal movement of the carriage 166 and motor 132, by operation of the motor 174, is effective to move the proximal end portion 54 (FIG. 5) of the core wire 56 longitudinally relative to the tubular outer member or sheath 58.

The handle 36 (FIGS. 2-4) has a generally cylindrical configuration and has a relatively small diameter. This facilitates manual gripping of the handle 36 and moving of the guidewire 44 longitudinally relative to the patient 32. The handle 34 can be manually rotated about its longitudinal central axis 134 to rotate the guidewire 44.

During this manual movement of the handle 36, the motors 132 and 174 may be maintained in a deenergized condition so that the configuration of the distal end portion 50 of the guidewire 44 is not changed. However, it may be desired to change the configuration of the distal or leading end portion 50 of the guidewire 44. If this is to be done, one or both of the motors 132 and/or 174 are energized to move the core wire 56 relative to the tubular outer member or sheath 58. This movement of the core wire 56 relative to the tubular outer member 58 is effective to change the configuration of the distal or leading end portion 50 of the guidewire 44. Changing the configuration of the distal or leading end portion 50 of the guidewire 44 may occur during manual longitudinal and/or rotational movement of the handle 36 to steer the guidewire along a tortuous path in the vascular system of the patient 32.

The housing 80 may be provided with knurling to facilitate manual gripping of the housing. If desired, the housing may be provided with longitudinally extending ribs in addition to or in place of the knurling. Circular ribs may be provided around the housing. Soft rubber polymeric sleeves may be provided on the housing 80 to facilitate gripping of the housing.

Manual movement of the handle 36 relative to the patient's body is facilitated by having the motors 132 and 174 disposed in a coaxial relationship with each other. By having the longitudinal central axes of the motors 132 and 174 coincident with the central axis 134 of the handle 36, the overall thickness, that is, the diameter, of the handle 36 is minimized. However, it is contemplated that the motors 132 and 174 may be mounted in a side-by-side or parallel relationship if desired. This would have the advantage of decreasing the overall length of the handle 36. However, it would tend to increase the thickness or the diameter of the handle.

In the illustrated embodiment of the handle, the motors 132 and 174 have rotatable output shafts 138 and 184. It is contemplated that either or both of the motors 132 and/or 174 may be linear motors having longitudinally moveable output members rather than rotary output members. If the first or distal motor 132 is replaced with a linear motor, a suitable drive arrangement would be provided to rotate the gripper 116 and the proximal end portion 54 of the core wire 56 relative to the housing 80 during operation of the linear motor.

Control Apparatus

A control apparatus 192 (FIG. 1) is provided to control the operation of the motors 132 and 174 (FIGS. 2-4). The control apparatus 192 includes a switch assembly 196 (FIGS. 1 and 7) which may be held by one of the hands, for example, the hand illustrated schematically at 40 in FIG. 1, of an individual utilizing the vascular guidewire system 30. In addition, the control apparatus 192 includes a control unit 200 (FIGS. 1 and 8).

In the illustrated embodiment of the invention, the control unit 200 is connected with the handle 36 and the motors 132 and 174 (FIGS. 3 and 4) by an electrical conductor or cable 204 (FIG. 1). The conductor or cable 204 may be referred to as a tether since it interconnects the control unit 200 and the handle 36. In the illustrated embodiment of the invention, a wireless connection is provided between a switch assembly 196 and the control unit 200. If desired, a wireless connection may be provided between a control unit 200 and the handle 36. Providing a wireless connection between the control unit 200 and the handle 36 would eliminate the conductor or cable 204.

Figure 8:
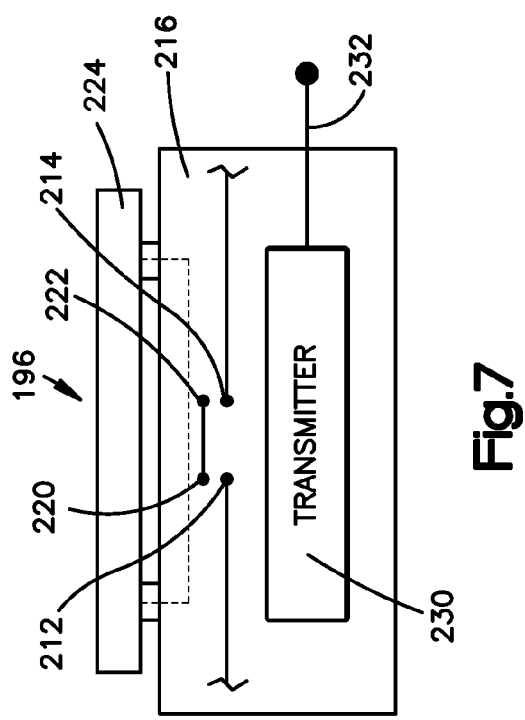
FIG. 8 is a schematic illustration of a control assembly which cooperates with the hand held switch assembly of FIG. 7 and forms part of the vascular guidewire system of FIG. 1.

The hand held switch assembly 196 is illustrated schematically in FIG. 7 and includes stationary switch contacts 212 and 214 which are disposed in a housing 216. Movable switch contacts 220 and 222 are connected to an actuator 224. The actuator 224 is manually movable relative to the housing 216 to move the movable switch contacts 220 and 222 from the open position illustrated schematically in FIG. 7 to the closed condition in which the movable contacts 220 and 222 engage the stationary switch contacts 212 and 214. When the movable switch contacts 220 and 222 engage the stationary switch contacts 212 and 214, a transmitter 230 in the housing 216 is energized to send a radio frequency signal from an antenna 232 (FIG. 7) to the control unit 200 (FIG. 8).

Figure 10:
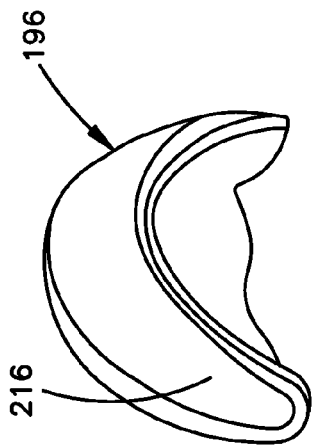
FIG. 10 is a schematic pictorial illustration, generally similar to FIG. 9, further illustrating the configuration of the hand held switch assembly.
Figure 9:
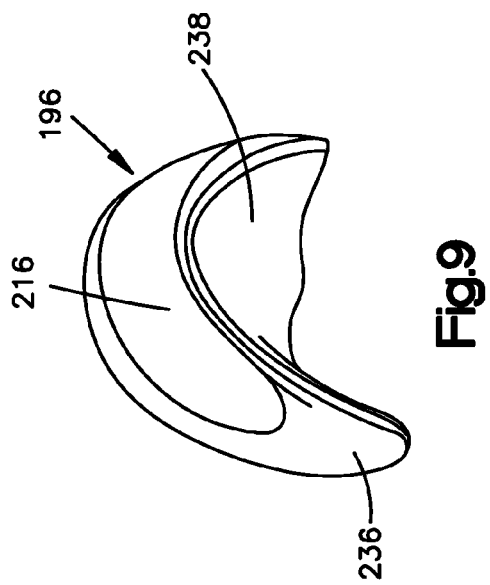
FIG. 9 is a schematic pictorial illustration depicting the configuration of the hand held switch assembly of FIG. 7.

To facilitate holding the hand held switch assembly 196 with one hand of an individual using the vascular guidewire system 30 in the manner illustrated schematically in FIG. 1, the hand held switch assembly may have a configuration corresponding to the configuration illustrated in FIGS. 9 and 10. In this specific embodiment of the invention, the switch housing 216 is formed of a resiliently deflectable polymeric material which can be manually compressed to move the moveable switch contacts 220 and 222 (FIG. 7) from the open condition to the closed condition.

The housing 216 includes a flange section 236 which extends from a main section 238 of the housing. The flange section 236 fits between the middle finger and ring finger on the hand 40 (FIG. 1) of the individual using the vascular guidewire system 30. The index fingers and middle fingers of a hand 40 holding the switch assembly 196 (FIGS. 1, 9 and 10) can be used to grip the handle 36. The ring finger and pinky fingers of the hand 40 can be used to grip the main section 238 of the switch assembly and to actuate the switch assembly 196 by compressing the housing 216.

Although it is believed that it may be desired to provide the hand held switch assembly 196 with the housing 216 having the configuration illustrated in FIGS. 9 and 10, it should be understood that the switch housing may have a different configuration if desired. For example, if the switch assembly 196 is not to be hand held, it is contemplated that the switch housing 216 may have a rectangular configuration, similar to the rectangular configuration illustrated schematically in FIG. 7. Alternatively, the switch assembly 196 may be disposed in the housing 80 of the handle or connector 36.

Figure 11:
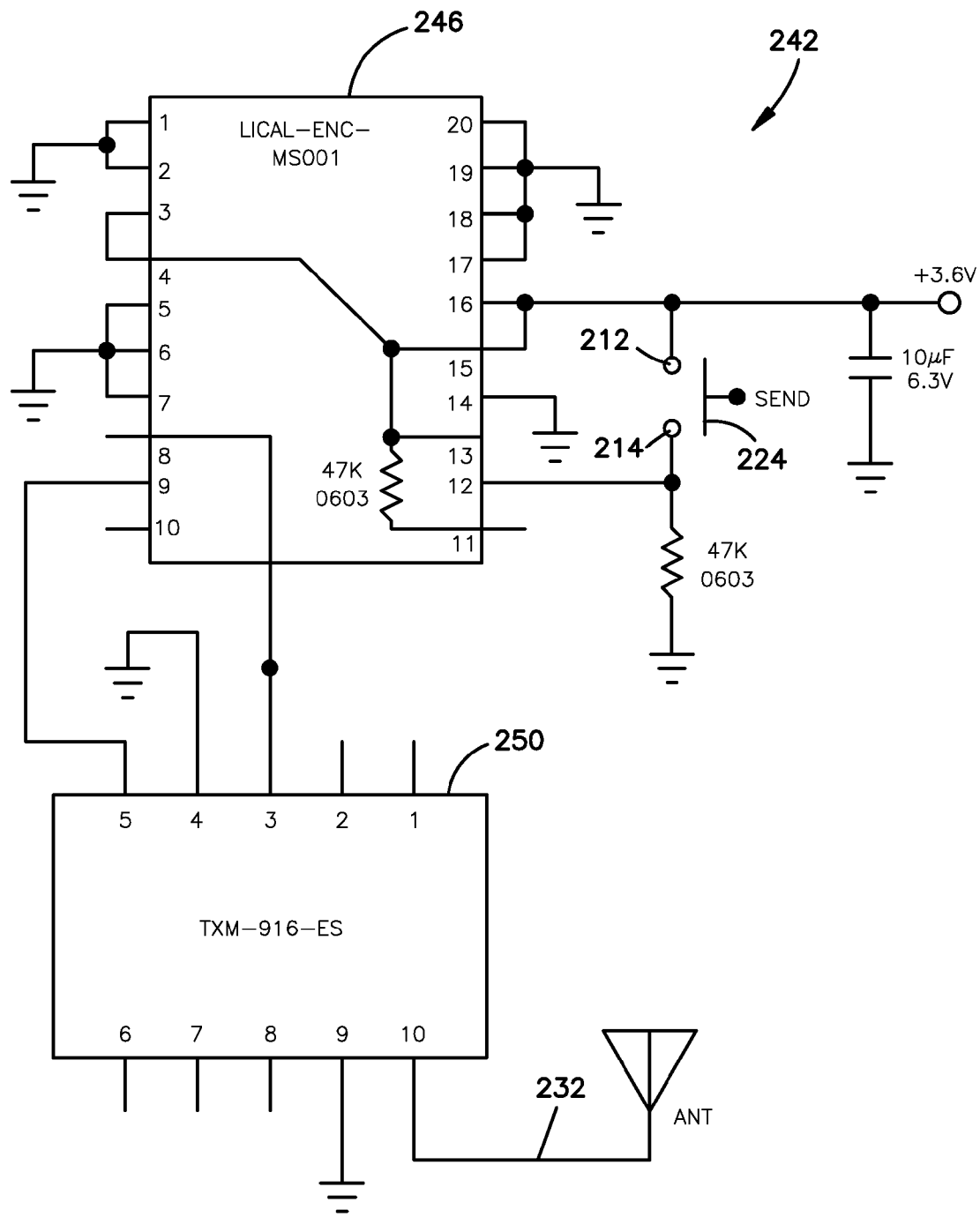
FIG. 11 is a schematic illustration of control circuitry used in association with the hand held switch assembly of FIG. 7.

Control circuitry 242 (FIG. 11) is used in the hand held switch assembly 196. The control circuitry 242 includes an MS Series Encoder/Decoder 246 which is commercially available from Linx Technologies, Inc. The encoder 246 is connected with a transmitter module 250 which is commercially available from Linx Technologies, Inc. The transmitter module 250 is connected to the antenna 232. It should be understood that encoders and/or transmitters having a different construction and/or available from a different source may be utilized if desired. When the actuator 224 (FIGS. 7 and 11) is manually actuated to complete a circuit across the stationary switch contacts 212 and 214, the transmitter module 250 (FIG. 11) is effective to transmit a signal to a receiver 260 (FIG. 8) in the control unit 200.

In addition to the receiver 260, the control unit 200 includes a battery 262 (FIG. 8) which is effective to energize the control unit 200, including control circuitry 264. An on-off switch 266 is connected with the control circuitry 264. In addition, a switch 268 controls the operation of translation control circuitry 270. The translation control circuitry 270 is connected with the second or proximal motor 174 (FIGS. 2 and 3) in the handle 236 by the conductor or cable 204. A switch 272 (FIG. 8) controls operation of the rotation control circuitry 274. The rotation control circuitry 274 is connected with and controls the operation of the first or distal motor 132 (FIGS. 2 and 4) in the handle 36.

A worm mode control switch 278 (FIG. 8) is operable to control worm mode circuitry 280. The worm mode circuitry 280 effects simultaneous operation of both the first or distal motor 132 (rotation) and the second or proximal motor 174 (longitudinal movement) (FIGS. 3 and 4). When the worm mode control circuitry 280 (FIG. 8) is activated by actuation of the control switch 278, both motors 132 and 174 are energized to effect simultaneous longitudinal movement and rotational movement of the proximal end portion 54 of the core wire 56. The simultaneous rotational and longitudinal movement of the proximal end portion 54 of the core wire 56 is effective to cause the distal end portion 50 of the guidewire 44 to continuously vary its configuration. This facilitates movement of the guidewire 44 through a blockage in a patient's vascular system with a rapid oscillatory or vibratory motion.

Oscillatory or vibratory motion of the distal end portion 50 of the guidewire 44 results from the configuration of the distal or leading end portion (FIG. 6) of the guidewire 44 continuously changing to effect combination of sideways and longitudinal deflection of the distal end portion of the guidewire. This combined oscillatory or vibratory movement of the distal or leading end portion 50 of the guidewire 44 is effective to enable the guidewire to move through a blockage or along a tortuous path in a patient's vascular system.

It is contemplated that the control unit 200 may have a construction which is different than the construction illustrated in FIG. 8. For example, the control unit 200 may be connected with the motors 132 and 174 in the handle 36 by a wireless transmitter rather than the conductor or cable 204. Alternatively, the control unit 200 may be built into the handle 36.

Figure 12:
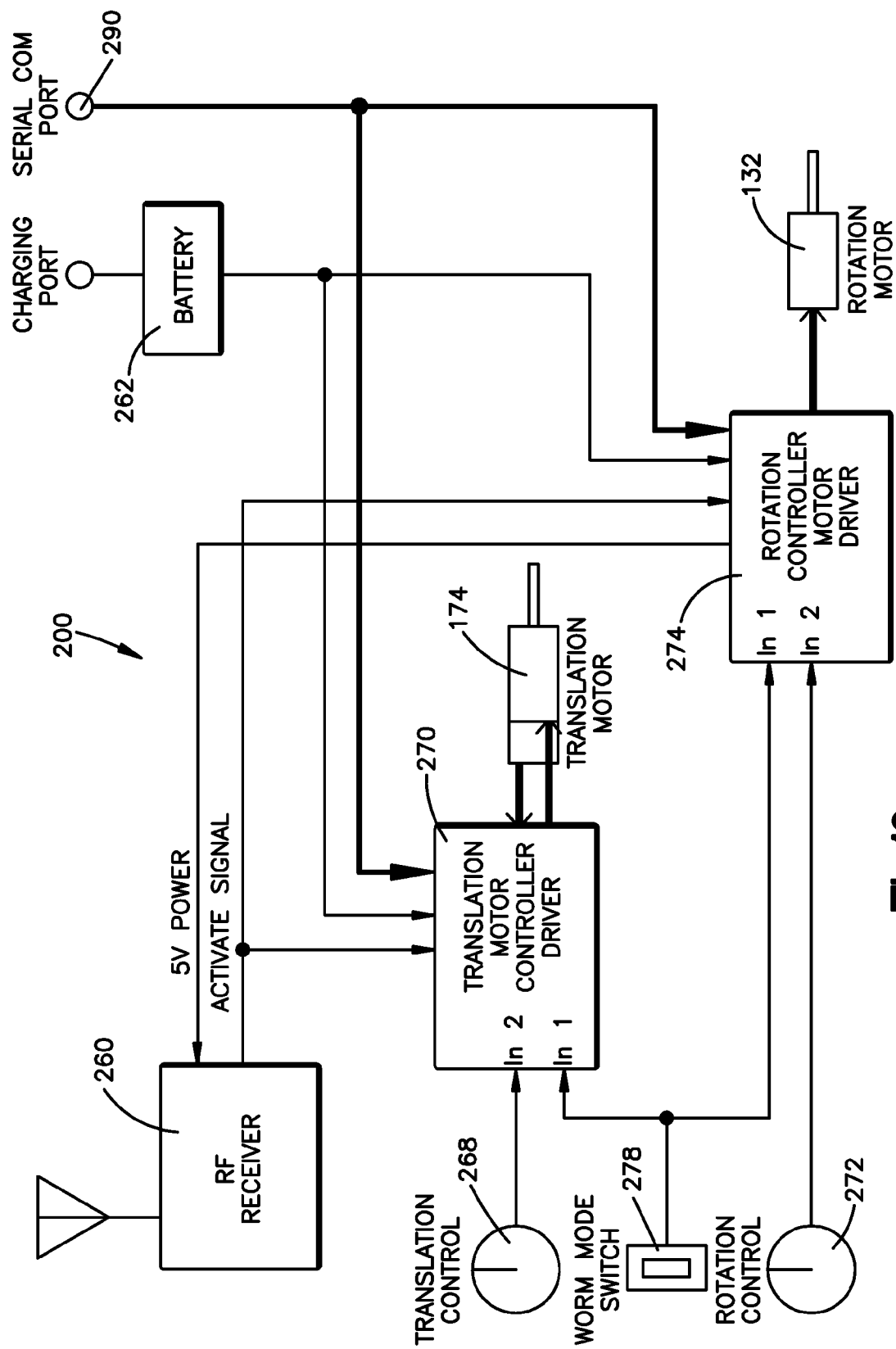
FIG. 12 is a schematic illustration depicting the relationship of components of the control assembly of FIG. 8 to other components of the vascular guidewire system of FIG. 1.

The relationship of the control unit 200 (FIG. 8) to the first and second motors 132 and 174 (FIGS. 2-4) is illustrated schematically in FIG. 12. When the receiver 260 in the control unit 200 (FIGS. 8 and 12) receives a signal from the transmitter 230 (FIG. 7) in the switch assembly 196, signals are transmitted from the receiver 260 (FIG. 8)*to* rotation motor control driver circuitry 274 (FIGS. 8 and 12) and to a translation motor control driver circuitry 270. Depending upon the programming of the control switches 272, 268 and 278 (FIG. 8), the translation motor control driver circuitry 270 (FIG. 12) and/or the rotation motor control driver circuitry 274 activate the rotation motor 132 and/or translation motor 174.

The extent of operation of the first or distal motor 132, that is, the rotation motor, is determined by the programming of the rotation control switch 272. Thus, the rotation control switch 272 functions as a program which may be set to have the output shaft 138 (FIG. 4) of the first rotation motor 132 rotate through a relatively small arcuate distance in either a clockwise or counterclockwise direction. Alternatively, the rotation control switch 272 may be programmed (set) to have the rotation motor controller drive circuitry 274 effect operation of the first or rotation motor 132 through a larger arcuate distance. Of course, the greater the arcuate distance through which output shaft 138 of the first motor 132 (FIG. 4) is rotated, the greater is the arcuate distance through which the proximal end portion 54 (FIG. 5) of the core wire 56 is rotated. It should be understood that the proximal end portion 54 of the core wire 56 may be rotated in either a clockwise or counterclockwise direction, as indicated by the arcuate arrows in FIG. 5, by operation of the first or rotation motor 132.

The extent of rotation of the proximal end portion 54 of the core wire 56 by the first or rotation motor 132 will effect the shape of the guidewire 44 in a very complex way. Rotating the proximal end portion of the core wire imparts potential energy which is stored in the core wire by resiliently deflecting the core wire in torsion about the longitudinal central axis of the core wire. The direction in which the proximal end portion 54 of the core wire 56 is rotated by operation of the first or rotation motor 132 will determine the direction in which the distal end portion 50 of the guidewire 44 is resiliently deflected in torsion and the direction in which the distal end portion of the guidewire is resiliently urged to move. The direction and extent of rotation of the proximal end portion 54 of the core wire 56 is determined by the programming of the rotation control switch 272. The rotation control switch 272 may be manually adjusted or programmed to provide any desired direction or extent of operation of the first or rotation motor 132.

If desired, an encoder may be associated with the first or rotation motor 132. The encoder would provide feedback to driver circuitry 274 to indicate the direction and extent of operation of the first or rotation motor 132. When the first or rotation motor 132 has been operated in a direction and to an extent corresponding to the programming of the rotation control switch 272, operation of the first or rotation motor 132 is interrupted.

Rather than initiating operation of the first or rotation motor 132, the signal from the transmitter 230 in the hand held switch assembly 196 (FIG. 7) to the receiver 260 in the control unit 200 (FIGS. 8 and 12) may initiate operation of the second or translation motor 174 (FIG. 12). Thus, if the translation control switch 268 is programmed to initiate operation of the translation motor 174 and the rotation control switch 272 is programmed to maintain the first or rotation motor 132 in a deenergized condition, the translation motor controller driver circuitry 270 (FIG. 12) will initiate operation of the second or translation motor 174. The direction and extent of operation of the second or translation motor 174 is determined by the position to which the translation control switch is preset.

If desired, an encoder may be associated with the second or translation motor 174 (FIG. 12). The encoder would provide feedback to the translation motor control driver circuitry 20 to indicate the direction and extent of operation of the second or translation motor 174. When the second or translation motor 174 has been operated in a direction and to an extent corresponding to the programming of the translation control switch 268, operation of the second or translation motor 174 is interrupted.

The translation control switch 268 can be programmed to have the output shaft 184 (FIG. 3) of the second or translation motor 174 rotate in either a clockwise or counterclockwise direction. If the output shaft 184 is rotated in a counterclockwise direction, the screw 176 (FIG. 3) is rotated in a counterclockwise direction to move the nut 178 toward the second or translation motor 174, that is, toward the left as viewed in FIG. 3. Similarly, if the translation control switch 268 (FIGS. 8 and 12) is preset to effect clockwise rotation of the output shaft 184 of the second or translation motor 174, the screw 176 is rotated in a clockwise direction. This results in movement of the nut 178 in a direction away from the second or translation motor 174, that is, toward the right as viewed in FIG. 3. The direction and extent of operation of the second or translation motor 174 is determined by the condition to which the translation control switch 268 is programmed.

The nut 178 is fixedly connected with the carriage 168 (FIG. 3) on which the first or rotation motor 132 (FIG. 4) is mounted. The gripper 116 is fixedly connected with the output shaft 138 of the first motor 132. Therefore, when the carriage 166 is moved along the central axis 134 of the handle 36 by rotation of the screw 176 (FIG. 3), the proximal end portion 54 of the core wire 56 is also moved along the central axis 134 of the handle 36. The greater the extent of rotation of the output shaft 184 (FIG. 3) of the second or translation motor 174, the greater is the rotation of the screw 176 and movement of the nut 178 along the screw. Of course, the greater the movement of the nut 178 along the screw 176 the greater is the extent to which the core wire 56 is moved relative to the tubular outer member or sheath 58.

Although the foregoing has described either the translation motor 174 or the rotation motor 132 as being operated in accordance with a predetermined program and in response to manual actuation of the switch assembly 196 (FIG. 7), it is contemplated that both the translation motor 174 and rotation motor 132 (FIG. 12) may be operated in response to a signal sent by the transmitter 230 to the receiver 260. If this is to be done, both the rotation control switch 272 and translation control switch 268 would be programmed to desired directions and extent of operation of the first or rotation motor 132 and second or translation motor 174. If this was done, the first or rotation motor 132 would be operated to rotate the proximal end portion 54 of the core wire 56 in a direction and to an extent corresponding to the programming of the rotation control switch 272. Similarly, the second or translation motor 174 would rotate the screw 176 to move the first or rotation motor 132 and the proximal end portion 54 of the core wire 56 through a distance and in a direction corresponding to the programming of the translation control switch 268. Once the two motors 132 and 174 have been operated to extents corresponding to the programming of the switches 272 and 268, operation of the motors 132 and 174 would be interrupted.

It is contemplated that the guidewire 44 may encounter a situation in which the previously described operation of the rotation motor 132 and/or translation motor 174 will not result in the guidewire moving to the desired position relative to the blood vessel. A worm control switch 278 (FIGS. 8 and 12) is provided to effect simultaneous operation of both the first or rotation motor 132 and the second or translation motor 174. Simultaneous operation of both of the motors 132 and 174 effects a oscillating rotation of the proximal end portion 54 of the core wire 56 and back and forth translational movement of the proximal end portion of the core wire. This results in a vibrating and oscillating resilient flexation of the leading or distal end portion 50 of the guidewire 44. This combined oscillatory and vibrational movement of the leading or distal end portion 50 of the guidewire 44 facilitates movement of the guidewire through and/or around an obstruction in a patient's vascular system.

The worm mode control switch 278 (FIG. 12) may be programmed to vary the extent of operation of either the first or rotation motor 132 or the second or translation motor 174.

This enables the worm mode switch 278 to be programmed to vary the magnitude of the vibratory and oscillatory movement of the distal end portion 50 of the guidewire 44 as the core wire 56 is simultaneously rotated by the first or rotation motor 132 and moved longitudinally by the second or translation motor 174.

The control unit 200 (FIG. 12) has a serial communication port 290 which enables an external computer to communicate with the translation motor controller driver circuitry 270 and the rotation motor controller driver circuitry 274 for the purpose of programming them. In addition, the serial communication port 290 enables control apparatus, corresponding to the switch assembly 196 and/or the control switches 266, 268, 272 and 278 to be located at a plurality of locations if desired. The manually actuated switch may be connected with the translation motor control driver circuitry 270 of FIG. 12 without having a wireless (radio frequency) transmission to the receiver 260. In addition, a second set of control switches, corresponding to the controls witches 266, 268, 272 and 278 may be provided to facilitate use of the vascular guidewire system 30.

Core Wire

In the embodiment of the invention illustrated in FIGS. 1-6, the core wire 56 has a circular cross sectional configuration throughout its length. The diameter of the core wire 56 remains constant from the proximal end of the core wire to the beginning of the distal or leading end portion 154 of the core wire. The core wire 56 may have a cross sectional configuration which is not circular. For example, the core wire may have an oval cross sectional configuration. As another example, the core wire 56 may have a polygonal cross sectional configuration.

The core wire 56 tapers in an axial direction at a plurality of locations in the distal end portion of the core wire, in the manner illustrated in FIG. 13. Thus, an axially outwardly and radially inwardly tapering section 296 extends from a relatively large diameter distal end of a cylindrical intermediate portion 300 to a cylindrical constant cross sectional configuration section 302. The cylindrical intermediate portion 300 extends between the proximal end portion 54 (FIG. 5) and the distal end portion 154 of the core wire 56. The intermediate portion 300 forms a major portion of the length of the core wire 56.

The tapering section 296 (FIG. 13) has a uniform taper throughout its length and has a configuration corresponding to the configuration of a portion of a right circular cone having a central axis which is coincident with a longitudinal central axis 72 of the core wire 56. A second tapering section 306 has the same conical configuration as the tapering section 296. The proximal end of the tapering section 306 has a circular cross sectional configuration with the same diameter as the diameter as the constant cross sectional configuration section 302. The second tapering section 306 tapers to a small diameter distal end which is connected to a second constant cross sectional section 308. The second constant cross sectional configuration section 308 has a cylindrical configuration. The second tapering section 306 has a configuration corresponding to the configuration of a portion of a right circular cone having a central axis which is coincident with the central axis 72 of the core wire 56.

In the embodiment of the core wire illustrated in FIG. 13, the diameter of portions of the core wire 56 are constant. Thus, the intermediate portion 300 and the two constant cross sectional configuration sections 302 and 308 have cylindrical configurations. The diameter of the tapering sections 296 and 306 constantly decreases in a direction toward the distal end of the core wire 56. Thus, the tapering sections 296 and 306 have diameters that decrease at a uniform rate in a direction toward the distal end of the core wire 56.

In the embodiment of the invention illustrated in FIG. 14, the core wire has alternating sections of a relatively small diameter and of a larger diameter. Since the embodiment of the invention illustrated in FIG. 14 is generally similar to the embodiment of the invention illustrated in FIGS. 1-13, similar numerals will be utilized to designate similar components, the suffix letter "a" being added to the numerals of FIG. 14 in order to avoid confusion. A core wire 56a has a constant diameter intermediate portion 300a. The intermediate portion 300a extends between distal end portion 154a and a proximal end portion (not shown).

The distal end portion 154a of the core wire 56a includes a first tapering section 296a. The first tapering section 296a has the configuration of a right circular cone and has a central axis which is coincident with a longitudinal central axis 72a of the core wire 56a. A first constant cross sectional configuration section 302a extends axially in a distal direction from the distal end of the tapering section 296a and has a circular cross sectional configuration.

In accordance with a feature of this embodiment of the core wire, a radially and axially outwardly flaring section 312 (FIG. 14) extends from the constant cross sectional configuration section 302a toward the distal end of the core wire 56a. The flaring section 312 has a configuration corresponding to the configuration of a right circular cone having its central axis disposed on the central axis 72a of the core wire 56a and having a base toward the distal end of the core wire 56a.

A second constant cross sectional configuration section 314 extends from the distal end of the flaring section 312 toward the distal end of the core wire 56a. The second constant cross sectional configuration section 314 has a uniform diameter throughout its length and has a cylindrical configuration. The diameter of the second constant cross sectional configuration section 314 is less than the diameter of the intermediate portion 300a.

A second tapering section 306a extends from the distal end of the second constant cross sectional configuration section 314 to a third constant cross sectional configuration section 308a. The third constant cross sectional configuration section 308a has a cylindrical configuration and has the same diameter as the first constant cross sectional configuration section 302a. However, the diameter of the third constant cross sectional configuration section 308a may be less than the diameter of the first constant cross sectional configuration section 302a. The first constant cross sectional configuration section 302a has a diameter which is less than the diameter of the second constant cross sectional configuration section 314. The diameter of the second constant cross sectional configuration section 314 is less than the diameter of the intermediate portion 300a.

By providing the axially tapering sections 296a and 306a, resilient bending of the distal end portion 154a of the core wire 56a is facilitated adjacent to the proximal and distal ends of the constant cross sectional configuration section 302a and adjacent to the proximal end of the third constant cross sectional configuration section 308a. To deflect the distal end portion of the core wire 56a, the core wire is subjected to either tension or compression forces.

By operating the second or proximal motor 174 (FIGS. 2 and 3) in either a forward or reverse direction, tension or compression forces can be exerted on the core wire 56a (FIG. 14). Thus, the second or proximal motor 174 is operated in a forward direction, the nut 178 is moved distally, that is, toward the right as viewed in FIG. 3, to move the first or distal motor 132 and second gripper toward the right (as viewed in FIG. 4). The outer tubular member or sheath 58 is held against movement by the distal or leading gripper 88. Therefore, the distal or rightward (as viewed in FIG. 4) movement of the second gripper 116 applies a compression force to the core wire 56.

Upon application of a compression force to either the core wire 56 or 56a, the force is transmitted through the core wire to the connection 62 (FIG. 6) between the distal end portion of the core wire and the distal end portion of the inner tubular member or sheath 58. When the central axis 72 (FIG. 6) or 72a (FIG. 14) of the core wire 56 or 56a is offset downward, as viewed in FIG. 6, from the central axis 66 of the tubular member 58, the application of compression force to the core wire 56 or 56a urges the distal end portion 60 of the guidewire 44 to deflect upwardly as viewed in FIG. 6.

Similarly, if the second or proximal motor 174 (FIG. 3) is operated in a reverse direction, the nut 178 is moved in a proximal direction, that is toward the left as viewed in FIG. 3. This results in tension forces being transmitted from the carriage 166 through the distal motor 132 to the gripper 116 and the core wire 56. The application of this leftward or proximally directed force to the core wire 56 or 56a, when the central axis 72 or 72a of the core wire is offset downward (as viewed in FIG. 6) from the central axis 66 of the tubular member or sheath 58, urges the tubular member or sheath to deflect downwardly, as viewed in FIG. 6. Thus, by operating the second or proximal motor 174 in a forward or reverse direction, the distal end portion 50 of the guidewire 44 may be urged to deflect either upward or downward, as viewed in FIG. 6. If the distal end portion 154 of the core wire 56 or 56a and the distal end portion 60 of the outer tubular member 58 are offset by 90 degrees about the central axis 66 of the outer tubular member 58, operation of the second or proximal motor 174 would urge the distal end portion 50 of the guidewire 44 to deflect either toward or away from a viewer, that is either in a direction into the plane of the sheet of drawings or out of the plane of the sheet of drawings.

In addition to being urged to deflect in a direction that is transverse to the central axis 66 of the outer tubular member sheath 58, the distal end portion 154 or 154a (FIGS. 13 and 14) of the core wire 56 or 56a may be resiliently deflected in torsion about the central axis 72 or 72a of the core wire 56 or 56a. To urge the distal end portion 154 or 154a of the core wire 56 or 56a to rotate about the central axis 72 or 72a of the core wire, the first or distal motor 132 (FIG. 4) is energized to rotate the second gripper 116 and the proximal end portion 54 of the core wire 56 or 56a about the central axis 72 or 72a of the core wire. This results in the distal end portion 154 or 154a of the core wire 56 or 56a (FIG. 13) being urged to rotate about the central axis 72 or 72a of the core wire 56 or 56a.

The distal end portion 154 or 154a (FIGS. 13 and 14) of the core wire 56 or 56a may be resiliently deflected in torsion (rotation) about the central axis 72 or 72a of the core wire 56 or 56a either before or after the distal end portion of the core wire has been urged to deflect by operation of the second or proximal motor 174 (FIG. 3) in either a forward or reverse direction. If desired, both motors 132 and 174 may be simultaneously operated to urge the distal or leading end portion 154 or 154a of the core wire 56 or 56a to deflect and rotate. Of course, rather than having simultaneous operation of the motors 132 and 174 (FIGS. 3 and 4), the motors may be operated sequentially.

The configuration to which the distal end portion 50 of the guidewire 44 moves in response to operation of the motors 132 and/or 174 is complicated and difficult to predict. This is because movement of the proximal end portion 54 of the core wire 56 relative to the tubular outer member or sheath results in the core wire being resiliently deflected to store energy. This stored energy functions as a spring force which is transmitted to the distal end portion 50 of the guidewire 44 through the core wire 56. The distal end portion 50 of the guidewire 44 is probably restrained, to at least some extent, against movement by body tissue. This makes it very difficult to accurately predict exactly what changes will occur in the configuration of the distal end portion 50 of the core wire 44 as a result of a given amount of operation of the motor 132 and/or the motor 174.

Force may be manually applied to the handle 36 during operation of the motors 132 and/or 174. Alternatively, the manual application of force to the handle 36 may be interrupted during operation of the motors 132 and 174. Thus, a longitudinally directed force may be manually applied to the handle 36 while operating either or both of the motors 132 and 174. Similarly, a rotational force may be manually applied to the handle 36 while operating either or both of the motors 132 and 174. Of course, the manual application of force to the handle 36 will further complicate predicting exactly what movement will be obtained at the distal end portion 50 of the guidewire 44 during operation of the motors 134 and/or 174.

Guidewire Configurations

By operating the motors 132 and 174 simultaneously and/or sequentially, various configurations may tend to be imparted to the guidewire 44. However, the actual guidewire configurations which are obtained during operation of the motors 132 and 174 when the guidewire 44 is in a patient's vascular system are the result of the complicated interaction of many different factors. If the motors 132 and/or 174 are operated to the same extent, a different guidewire configuration will be obtained when the core wire 56 is used than when the core wire 56a is used.

The following are simplified predictions as to changes which may tend to occur in the configuration of the distal end portion 50 of the guidewire 44 in response to operation of the motors 132 and/or 174. It should be understood that these simplified predictions are being made for purposes of explaining how the components of the handle 36 and guidewire 54 cooperate with each other. When the guidewire 44 is being used with a patient 32, predicting how the configuration of the distal end portion 50 of the guidewire will change with operation of the motors 132 and/or 174 is far more complicated.

Assuming that the distal or leading end portion 50 of the guidewire 44 is in the position illustrated in FIG. 6 relative to a viewer of the various guidewire configurations illustrated in FIGS. 15A-15D, the second or proximal motor 174 (FIG. 3) is operated in a direction to move the nut 178 toward the motor, that is toward the left or proximal end of the handle 36. As this occurs, tension forces are transmitted from the nut 178 through the carriage 166 and first or distal motor 132 to the second gripper 116 which securely holds the proximal end portion 54 of the guidewire 56. The application of tension forces to the guidewire 56 by movement of the nut 178 toward the second or proximal motor 174 (FIG. 3), tensions the core wire 56. Tensioning the core wire 56 tends to urge the guidewire 44 to resiliently deflect the distal or leading end portion 50 of the guidewire downward in the manner illustrated schematically at 320 in FIG. 15A.

Assuming downward deflection of the distal end portion 50 of the guidewire 44 occurs, a curved configuration is imparted to the guidewire. This curved configuration may be referred to as a "hockey stick" configuration And is illustrated in FIG. 15A.

However, if the translation control switch 268 (FIGS. 8 and 12) is actuated to effect operation of the second or proximal motor 174 in a forward direction to move the nut 178 in a distal direction, that is, toward the right as viewed in FIG. 3, compression forces are transmitted from the nut through the carriage 166 and first or distal motor 132 to the proximal end portion 54 of the guidewire 56. Assuming that the distal end portion 50 of the guidewire 44 is in the position illustrated in FIG. 6, the application of compression forces, that is rightwardly directed forces as viewed in FIG. 6, would result in the distal end portion of the guidewire 44 being resiliently deflected upwardly, rather than downwardly, in the manner illustrated at 320 in FIG. 15A.

To impart the configuration illustrated schematically at 320 in FIG. 15A to the distal end portion 50 of the guidewire 44, the translation control switch 268 (FIGS. 8 and 12) is actuated to effect operation of the proximal motor 174 and proximal movement of the nut 178, that is, movement of the nut toward the left as viewed in FIG. 3. This operation of the second or proximal motor 174 occurs in response to manual actuation of the switch assembly 196 (FIG. 7). The leftward (as viewed in FIG. 3) movement of the nut 178 results in the transmission of tension forces through the carriage 166 and first or distal motor 132 to the second gripper 116 and the proximal end portion 54 of the core wire 56.

These tension forces are transmitted through the core wire 56 to the connection 62 (FIG. 6). Since the connection 62 is offset downwardly (as viewed in FIG. 6) from the longitudinal central axis 66 of the outer tubular member or sheath 58, the tension forces cause the distal end portion 50 of the guidewire 44 to tend to resiliently bend downward (as viewed in FIG. 6). This may result in the configuration illustrated schematically at 320 in FIG. 15A being imparted to the guidewire 44. The guidewire configuration illustrated at 320 in FIG. 15A may be referred to as a "hockey stick" configuration.

It is contemplated that it may be desired to impart a greater degree of resilient deflection to the distal end portion 50 of the guidewire 44 than is obtained with the "hockey stick" configuration illustrated at 320 in FIG. 15A. When this is to be done, the translation control switch 268 (FIGS. 8 and 12) is actuated to a preprogrammed position corresponding to a larger amount of operation of the proximal motor 174 in response to actuation of the switch assembly 196. When the switch assembly 196 (FIG. 7) is manually actuated, the nut 178 (FIGS. 1 and 3) is moved toward the left, that is, proximally. The increased proximal movement of the nut 178 increases the tension forces which are transmitted through the core wire 56 to the connection 62 (FIG. 6) between the core wire and the outer tubular member or sheath 58.

In addition, the rotation control switch 272 (FIGS. 8 and 12) is actuated to a preprogrammed position corresponding to a desired amount of operation of the distal (rotation) motor 132 (FIGS. 2, 4 and 12) and torsional deflection of the core wire 56. Therefore, when the switch assembly 196 (FIG. 7) is manually actuated, the gripper 116 (FIG. 4) is rotated. This results in the core wire 56 being resiliently deflected under the effect of both longitudinal and rotational movement of the gripper 116. This results in the application of combined torsional (rotational) and tension (translational) deflection of the core wire 56. This may result in the guidewire 44 tending to have the configuration illustrated at 324 in FIG. 15B. This configuration may be referred to as a "Cobra I" configuration. This configuration can only be obtained with combined rotational and translational deflection of the guidewire 56 as a result of operation of both motors 132 and 174.

It is contemplated that it may be desired to deflect the distal end portion 50 of the guidewire 44 to even a greater extent, in the manner illustrated schematically 326 in FIG. 15C. When it is desired to obtain the relatively large extent of deflection illustrated at 326 in FIG. 15C, the translation control switch 268 is programmed to effect operation of the second or proximal motor 174 to rotate the output shaft 184 through a relatively large distance in response to manual actuation of the switch assembly 196. When this occurs, the nut 178 is moved through a relatively large distance toward the proximal motor 174 to increase the tension forces and extent of resilient deflection of the distal end portion 154 of the core wire 56.

In addition, the rotation control switch 272 (FIGS. 8 and 12) is programmed to effect operation of the first or distal (rotation) motor 132 (FIGS. 2, 4, and 12) to rotate the gripper 116 and the proximal end portion 54 of the guidewire 56 through a relatively large distance in response to manual actuation of the switch assembly 196. The application of relatively large combined torsional (rotational) and tension (translational) deflection of the core wire 56 results in the guidewire 44 tending to have the configuration illustrated at 326 in FIG. 15C. This configuration may be referred to as "Cobra II" configuration. The "Cobra II" configuration can only be obtained with combined rotational and translational deflection of the guidewire 56 as a result of operation of both motors 132 and 174.

If it is desired to obtain the configuration illustrated at 328 in FIG. 15D, the core wire 56a of FIG. 14 may be used in the guidewire 44. The core wire 56a has two relatively thin sections, that is, the constant cross sectional configuration section 302a and the constant cross sectional configuration section 308a adjacent to the distal end of the core wire. The motor 174 (FIGS. 2 and 3) is operated in a forward direction to rotate the screw 176 to move the nut 178 toward the left, that is, toward the second or proximal motor 174. The resulting tension in the core wire 56a results in resilient deflection occurring at both of the reduced diameter sections 308a and 302a of the core wire 56a. In addition, the motor 132 is operated to resiliently deflect the core wire 56a in torsion. The resulting configuration of the guidewire 44 may be referred to as a "swan neck" configuration.

It should be understood that the extent of operation of the first or distal motor 132 (FIG. 4) and second or proximal motor 174 (FIG. 3) is controlled by the programming of the control switches 268 and 272 (FIGS. 8 and 12). The control switches 268 and 272 are manually set to conditions corresponding to the desired extent of operation of the motors 132 and 174 (FIGS. 2-4). After the control switches 268 and 272 have been programmed to positions corresponding to the desired extent of operation of the motors 132 and 174, manual actuation of the switch assembly 196 (FIG. 7) results in a signal being transmitted to the control unit 200 to effect operation of the motors 132 and 174 (FIGS. 2-4) to the programmed extent. Operation of the motors 132 and 174 is then effective to resiliently deflect the distal or leading end portion 50 of the guidewire 44 to the desired extent. By manually programming the control switches 268 and 272 (FIGS. 8 and 12), any one of the configurations illustrated in FIG. 15A-15D can be obtained. Programming of the rotation control switch 272 for the motor 132 controls the extent of rotational movement of the distal or leading end portion 50 of the guidewire 44 about the central axis 72 of the core wire 56.

When the switch assembly 196 (FIG. 7) is manually released, the switch contacts 220 and 222 (FIG. 7) move away from the stationary switch contacts. When this occurs, the motors 132 and 174 (FIGS. 2-4) are deenergized. The control switches 268, 272 and 278 are then manually reprogrammed to positions corresponding to the initial configuration of the guidewire 44. Subsequent actuation of the switch assembly 196 results in operation of the motors 132 and 174 to return the distal end portion 50 of the guidewire 44 to its initial or undeflected condition. Of course, the guidewire 44 may be maintained in its deflected condition if desired.

The control switches 268, 272 and 278 may be reprogrammed to positions corresponding to a different configuration of the guidewire 44. Thus, the control switches 268, 272 and 278 may first be programmed to effect operation of the motors 132 and 174 to deflect the guidewire 44 to the "hockey stick" configuration of FIG. 15A. The control switches 268, 272 and 278 may subsequently be programmed to effect operation of the motors 132 and 174 to change the configuration of the guidewire 44 from the "hockey stick" configuration of FIG. 15A to the "Cobra 2" configuration of FIG. 15.

A computer may be utilized in place of the manually settable switches 268, 272, and 278. The computer is programmed to effect operation of the motors 132 and 174 to change the configuration of the guidewire 44 to any one of a plurality of preprogrammed configurations. These preprogrammed guidewire configurations would include the configurations illustrated in FIGS. 15A-15D and additional configurations. An individual using the vascular guidewire system 30 (FIG. 1) would merely press an input button or other member to select the program corresponding to the desired configuration of the guidewire 44.

Alternative Embodiment

In the embodiment of the invention illustrated in FIGS. 1-15, electric motors 132 and 174 (FIGS. 2-4) having rotatable output shafts 138 and 184 are utilized to effect movement of the core wire 56 (FIG. 5) relative to the tubular outer member or sheath of the guidewire 44. In the embodiment of the invention illustrated in FIGS. 16-19, shape-memory material is utilized as linear motors to effect movement of a core wire 56 relative to an outer tubular member or sheath 58 of a guidewire 44. The shape-memory material motors of the embodiment of FIGS. 16-19 cooperates with a guidewire having the same construction and mode of operation as the guidewire 44 of FIGS. 1-15.

A vascular guidewire system 336 (FIG. 16) includes a handle or connector 338 (FIGS. 16 and 17) which is manually grasped with both hands, corresponding to the hands 38 and 40 of FIG. 1. Force is manually applied to the handle or connector 338 to move a guidewire 340 relative to a patient in the same manner as previously explained in conjunction with the guidewire 44 and patient 32 of FIG. 1. Thus, manual force is applied to the handle 338 to move the guidewire longitudinally (axially) relative to the patient. Similarly, manual force is applied to the handle 338 to rotate the guidewire 340 and handle relative to the patient.

In accordance with a feature of the embodiment of the invention illustrated in FIGS. 16-19, shape-memory material is utilized to form motors which actuate a guidewire to change the configuration of a distal end portion of the guidewire. The shape-memory material may be a nickel-titanium alloy, such as "Nitinol". However, other known shape-memory materials, such as copper-zinc-aluminum-nickel or copper-aluminum, nickel alloy, may be used. The shape-memory alloy undergoes deformation at one temperature and then recovers its original, undeformed shape upon heating above its "transformation" temperature. Although a one-way shape-memory material is used in the embodiment of the invention illustrated in FIGS. 16-19, a two-way shape-memory material may be used if desired.

In the embodiment of the invention illustrated in FIGS. 16-19, a shape-memory material actuator or motor 344 (FIG. 16) is used to move a proximal portion of a core wire 346 longitudinally relative to an outer tubular member or sheath 348 of the guidewire 340. The guidewire 340 has the same construction and mode of operation as the guidewire 44 of FIGS. 1-15. A proximal end portion 352 of the outer tubular member or sheath 348 is held against movement relative to the handle or connector 338 by a gripper 354. Although the gripper 354 has been illustrated schematically in FIG. 16, it should be understood that the gripper 354 may have the same construction as the gripper 88 of FIG. 4. The gripper 354 securely holds the outer tubular member or sheath 348 against movement relative to the handle or connector 348 during rotational and/or axial movement of the core wire 346 relative to the outer tubular movement or sheath 348.

The vascular guidewire system 336 (FIG. 16) includes a second shape-memory material actuator or motor 360. The second shape-memory material actuator 360 is used to rotate the proximal end portion 364 of the core wire 346 relative to the outer tubular member or sheath 348. The proximal end portion 364 of the core wire 346 extends axially outwardly from the outer tubular member 348 and is securely held by a second gripper 368 (FIG. 18).

The second gripper 368 has the same general construction as the second gripper 116 of FIG. 4. However, it should be understood that the second gripper 368 of FIG. 18 may have a different construction if desired. The second gripper 368 is effective to transmit force from the first linear shape-memory material actuator 344 (FIG. 16) to the proximal end portion 364 of the core wire 346 and/or to transmit force from the second linear shape-memory material actuator 360 to the proximal end portion 364 of the core wire 346.

The force transmitted force from the first linear shape-memory material actuator 344 (FIG. 16) to the second gripper 368 (FIG. 18) effects translational or longitudinal movement of the proximal end portion 364 of the core wire 346 relative to the outer tubular member or sheath 348. Force transmitted from the second linear shape-memory material actuator 360 (FIG. 16) to the second gripper 368 effects rotational movement of the proximal end portion 364 of the core wire 346 relative to the outer tubular member or sheath 348. Transmitting force from both the shape-memory material actuator 344 and shape-memory material actuator 360 to the proximal end portion 364 of the core wire 346 results in combined rotational and translational movement of the proximal end portion 364 of the core wire 346 relative to the proximal end portion 352 of the outer tubular member or sheath 348.

The force transmitted from the first shape-memory material actuator 344 (FIG. 16) to the core wire 346 of the guidewire 340 corresponds to the force transmitted from the motor 174 (FIG. 3) to the core wire 56 (FIGS. 4 and 5) of the guidewire 44. The force transmitted from second shape-memory material actuator 360 (FIG. 16) to the core wire 346 of the guidewire 340 corresponds to the force transmitted from the 132 (FIG. 4) to the core wire 56 of the guidewire 44. The shape-memory material actuators 344 and 360 (FIG. 16) are linear motors which correspond to the motors 174 and 132 (FIGS. 3 and 4).

As was previously explained in conjunction with the embodiment of the invention illustrated in FIGS. 1-15, axial and/or rotational movement of the proximal end portion 364 (FIGS. 16 and 18) of the core wire 346 relative to the outer tubular member 348 tends to urge deflection of the distal end portion (not shown) of the guidewire 340. It should be understood that the distal end portion of the guidewire 340 has the same construction as the distal end portion 50 of the guidewire 44 (FIG. 6). Thus, the distal end portion of the core wire 346 (FIGS. 16 and 18) is fixedly connected with the distal end portion of the outer tubular member or sheath 348 by a connection corresponding to the connection 62 of FIG. 6.

Although the core wire 346 (FIGS. 16 and 18) has the same configuration as the core wire 56 of FIG. 13, it should be understood that the core wire 346 may have a configuration corresponding to the configuration of the core wire 56a of FIG. 14.

When the first linear shape-memory material actuator 344 (FIG. 16) is heated to a temperature above the temperature range at which the transformation from martensite to austenite occurs, the first linear shape-memory material actuator 344 shortens in overall length. A distal end portion 372 of the linear shape-memory material actuator 344 is fixedly secured to a carriage 376 on which the second gripper 368 (FIG. 18) is disposed.

When the first linear shape-memory material actuator 344 is heated and shortens in length, the carriage 376 is moved in a proximal direction, that is, toward the left as viewed in FIG. 16. This results in movement of the proximal end portion 364 of the core wire 346 in a proximal direction relative to the proximal end portion 352 of the outer tubular member or sheath 348. Since the distal end portion of the core wire 346 is fixedly connected to the distal end portion of the outer tubular member or sheath 348, this translational movement of the proximal end portion 364 of the core wire 346 relative to the proximal end portion 352 of the outer tubular member or sheath 348 causes the distal end portion of the guidewire to resiliently deflect in the same manner as was previously explained in conjunction with the guidewire 44 of FIGS. 5 and 6.

When the second linear shape-memory material actuator 360 (FIG. 16) is heated to a temperature above its transformation temperature, the overall length of the actuator is decreased. Decreasing the over length of the actuator 360 causes a drive assembly 380 (FIGS. 16, 18 and 19) to effect rotational movement of the proximal end portion 364 (FIG. 18) of the core wire 346 relative to the proximal end portion 352 of the outer tubular member or sheath 348. The actuators 344 and 360 (FIG. 16) can be simultaneously heated to effect simultaneous rotation and longitudinal movement of the proximal end portion 364 of the core wire 346 relative to the proximal end portion 352 of the outer tubular member or sheath 348 of the guidewire 340. Alternatively, the actuators 344 and 360 can be sequentially heated to effect sequential rotation and longitudinal movement of the proximal end portion 364 of the core wire 346.

The drive assembly 380 includes a screw 384 (FIGS. 16, 18 and 19) having helical thread convolutions 386 which cooperate with helical thread convolutions formed in a main section 388 of the handle 338. The helical thread convolutions 386 have a relatively large pitch and lead. The relatively large pitch and lead of the helical thread on the screw 384 enables the screw to be readily moved axially relative to the main section 388 of the handle 338 by pulling on the screw with the second linear shape-memory material actuator 360.

When the screw 384 is moved axially relative to the main section 388 of the handle or connector 338 by the second actuator 360, the helical thread convolution 396 on the screw 384 slides along the internal thread convolution on the main section 388 of the handle 338. As this occurs, the screw rotates about its longitudinal central axis. The longitudinal central axis of the screw 384 is coincident with the longitudinal central axis of the proximal end portion 364 of the core wire 346.

The carriage 376 has a pair of radially extended flanges 392 and 394 (FIG. 19). The flanges 392 and 394 on the carriage 376 block relative rotation between the carriage and screw 384. Therefore, when the screw 384 is rotated by the shortening of the second linear shape-memory material actuator 360, the gripper 368 and carriage 376 rotate with the screw. This rotates the proximal end portion 364 of the core wire 346.

The proximal end of the linear shape-memory material actuator 360 is anchored to a brace or partition 400 (FIG. 16) in the handle 338. The distal end of the linear shape-memory metal actuator 360 is fixedly connected to the screw 384. Similarly, the proximal end of the linear shape-memory material actuator 344 is fixedly connected to a brace or partition 404 in the handle 338. The distal end portion 372 of the linear shape-memory material actuator 344 is fixedly connected to the carriage 376.

Conductors 410 (FIG. 16) from a cable 416 are connected with linear shape-memory metal actuators 344 and 360. The cable 416 is connected with a control unit, corresponding to the control unit 200 of FIG. 8. Rather than providing electrical current to operate the motors 132 and 174 (FIGS. 3 and 4), in the embodiment of the invention illustrated in FIGS. 16-19, the control unit 200 (FIG. 8) is connected with the cable 416 (FIG. 16). In the embodiment of FIGS. 16-19, the control unit 200 (FIG. 8) provides current to activate the linear shape-memory metal actuators 344 and 360 by heating them.

The current conducted from the cable 416 to the linear shape-memory material actuators 344 and 360 is effective to heat the actuators through their transformation temperature ranges so that they are activated to recover their original, undeformed shape which is shorter than the shape shown in FIG. 16. As this occurs, the first linear shape-memory material actuator 344 pulls the carriage 376 distally, that is, toward the left as viewed in FIG. 16. As this occurs, the proximal end portion 364 of the core wire 346 is moved longitudinally relative to the outer tubular member or sheath 348. As the second linear shape-memory metal actuator 360 is heated through its transformation temperature range and its overall length decreases, the screw 384 is pulled in a distal direction, that is toward the left as viewed in FIG. 16. As this occurs, the helical thread convolution 386 causes the screw 384 to rotate relative to the main section 388 of the handle 338. This effects rotation of the core wire 346 relative to the outer tubular member or sheath 348.

The carriage 376 and screw 384 are urged toward their initial positions by biasing springs 422 and 424. The biasing spring 422 urges the carriage 376 toward its initial position. The biasing spring 424 urges the screw 384 toward its initial position.

When the linear shape-memory material actuators 344 and 360 are cooled from temperatures above their transformation temperature ranges to temperatures below their transformation temperature ranges the actuators are stretched back to their initial length illustrated in FIG. 16. This stretching of the shape-memory material actuators back to their initial lengthy occurs under the influence of force provided by the springs 422 and 424. In addition, force is transmitted from the resiliently deflected guidewire 340 to urge the carriage 376 and screw 384 toward their initial positions.

Conclusion

In view of the foregoing description, it is apparent that the present invention provides an improved vascular guidewire system 30. The guidewire system includes a handle 36 which is connected with a tubular member or sheath 58. The tubular member 58 at least partially encloses a core wire 56. Forces are manually applied to the handle 36 to rotate and/or move the guidewire 44 along a blood vessel in a vascular system.

The configuration of a distal end portion 60 of the tubular member or sheath 58 of the guidewire 44 is changed by operating first and/or second motors 132 and 174 in the handle 36. The first motor 132 may be operated to rotate the core wire 56 relative to the tubular member or sheath 58. The second motor 174 may be operated to move the core wire 56 longitudinally relative to the tubular member or sheath 58. The motors 132 and 174 in the handle 36 may advantageously be disposed in a coaxial relationship.

The present invention has a plurality of features which may be utilized together in the manner disclosed herein. Alternatively, the various features of the invention may be used in different in combinations with each other and/or features from the prior art.

Having described the invention, the following is claimed:

1. A vascular guidewire system comprising, a tubular member which at least partially encloses a core wire, an elongated housing, a first gripper connected with said housing to grip a proximal end portion of said tubular member to hold said proximal end portion of said tubular member against movement relative to said housing, a second gripper disposed in said housing to grip a proximal end portion of said core wire, a first motor having a first axis of rotation, said first motor being disposed in said housing and connected with said second gripper, said first motor being operable to rotate said second gripper and said proximal end portion of said core wire relative to said housing about said first axis of rotation while said first gripper holds the proximal end portion of said tubular member against movement relative to said housing, and a second motor disposed in said housing in a coaxial relationship with said first motor, said second motor having a second axis of rotation which is coincident with said first axis of rotation, said second motor being operable to move said first motor and said second gripper relative to said housing along the second axis of rotation while said first gripper holds the proximal end portion of said tubular member against movement relative to said housing and while said second gripper holds the proximal end portion of said core wire.

2. A guidewire system as set forth in claim 1 further including a carriage disposed in said housing, said first motor and said second gripper being disposed on said carriage, a drive member connected with said carriage and said second motor, said drive member being rotatable about the axis of rotation of said second motor by said second motor to move said carriage and said first motor relative to said housing and said tubular member.

3. A vascular guidewire system as set forth in claim 1 further including a drive screw disposed in said housing and connected with said second motor, said drive screw being rotatable about an axis which is coincident with said second axis of rotation by operation of said second motor, an internally threaded member connected with said first motor and disposed in engagement with an external thread on said drive screw, said internally threaded member and said first motor being movable along the second axis of rotation upon operation of said second of said second motor.

4. A vascular guidewire system as set forth in claim 1 further including a control unit connected with said housing by an elongated flexible conductor to enable said housing to be readily moved relative to said control unit, said control unit containing at least one selectively actuatable program for operation of at least one of said motors.

5. A vascular guidewire system as set forth in claim 1 further including a connector which fixedly connects a distal end portion of said core wire to a distal end portion of said tubular member.

6. A vascular guidewire system as set forth in claim 1 wherein said core wire has a distal end portion which is fixedly connected to a distal end portion of said tubular member, said distal end portion of said core wire includes a first portion which tapers in an axial direction toward a distal end of said core wire from a first cross sectional area to a second cross sectional area which is smaller than the first cross sectional area, a second portion which is located distally of said first portion and flares in an axial direction toward a distal end portion of said core wire from a third cross sectional area to a fourth cross sectional area which is greater than the third cross sectional area, a third portion which is located distally of said second portion and tapers in an axial direction toward a distal end of said core wire from a fifth cross sectional area to a sixth cross sectional area which is smaller than the fifth cross sectional area.

7. A vascular guidewire system for use in a vascular system of a patient's body, said guidewire system comprising an elongated tubular member having proximal and distal end portions, an elongated core wire at least partially disposed within said tubular member, said core wire having a distal end portion which is fixedly connected to said distal end portion of said tubular member, said core wire having a proximal end portion which extends outward from said proximal end portion of said tubular member, a first gripper which grips said proximal end portion of said tubular member, a second gripper which grips said proximal end portion of said core wire, a first motor which is connected with said second gripper and is operable to rotate said second gripper and said proximal end portion of said core wire relative to said first gripper and said proximal end portion of said tubular member while said distal end portion of said core wire is fixedly connected to said distal end portion of said tubular member, a second motor which is connected with said proximal end portion of said core wire and is operable to move said proximal end portion of said core wire longitudinally relative to said first gripper and said proximal end portion of said tubular member while said distal end portion of said core wire is fixedly connected to said distal end portion of said tubular member.

8. A vascular guidewire system as set forth in claim 7 wherein said first motor has an output member with an axis of rotation which is coincident with an axis about which said first gripper and said proximal end portion of said core wire are rotatable, said second motor having an output member with an axis of rotation which is coincident with the axis of rotation of said first motor.

9. A vascular guidewire system as set forth in claim 8 further including a housing which encloses said first and second motors and has a central axis which is coincident with the axes of rotation of said first and second motors.

10. A vascular guidewire system as set forth in claim 7 further including a housing enclosing said first and second motors, a control unit connected with said housing and said first and second motors by an elongated flexible conductor to enable said housing to be readily moved relative to said control unit, and a manually actuatable switch containing a transmitter which transmits a signal to said control unit to initiate a control function in response to actuation of said switch.

11. A vascular guidewire system as set forth in claim 10 wherein said switch includes a housing to be held in a human hand, said housing having a first portion to be engaged by the pinky and ring fingers on the human hand and a flange portion which is disposed at one end of said housing and extends outward from said first portion of said housing to enable said flange portion to be held between the ring and middle fingers of the human hand.

12. A vascular guidewire system as set forth in claim 7 wherein said distal end portion of said core wire is fixedly connected to said distal end portion of said tubular member at a location offset to one side of a longitudinal central axis of said tubular member.

13. A vascular guidewire system a set forth in claim 7 further including an intermediate tubular member which extends around at least a portion of the distal end portion of the core wire, said second gripper engages said intermediate tubular member.

14. A method of moving a guidewire in a vascular system of a patient's body, said method comprising the steps of providing a guidewire which includes a tubular member which at least partially encloses a core wire and a handle which is connected with the tubular member and core wire, manually applying a longitudinally directed force to the handle to move the tubular member and core wire along a blood vessel in the vascular system, manually applying a rotational force to the handle to rotate the tubular member and core wire relative to a blood vessel in the vascular system, changing the configuration of a distal end portion of the tubular member by operating a first motor in the handle to rotate a proximal end portion of the core wire relative to a proximal end portion of the tubular member while distal end portions of the tubular member and core wire are fixedly interconnected, and changing the configuration of the distal end portion of the tubular member by operating a second motor in the handle to move the proximal end portion of the core wire along a longitudinal central axis of the proximal end portion of the core wire while the distal end portions of the tubular member and core wire are fixedly interconnected.

15. A method as set forth in claim 12 wherein said step of operating a first motor to rotate a proximal end portion of the core wire includes rotating the proximal end portion of the core wire about a first axis, said step of operating a second motor includes rotating an output shaft of the second motor about the first axis.

16. A method as set forth in claim 15 wherein said step of manually applying a rotational force to the handle to rotate the tubular member and core wire includes rotating the first and second motors about the first axis.

17. A method as set forth in claim 14 wherein said steps of manually applying a longitudinally directed force to the handle and manually applying a rotational force to the handle are at least partially preformed while manually holding a switch, said method further includes manually actuating the switch to initiate operation of at least one of said first and second motors.

18. A method as set forth in claim 14 further including the step of simultaneously operating the first and second motors to effect simultaneous rotation and longitudinal movement of the proximal end portion of the core wire relative to the proximal end portion of the tubular member.

19. A method as set forth in claim 18 wherein said step of manually applying a longitudinally directed force to the handle is at least partially performed during simultaneous operation of the first and second motors.

20. A method as set forth in claim 14 wherein said step of operating a first motor in the handle is at least partially performed while manually applying a longitudinally directed force to the handle.

21. A method as set forth in claim 14 wherein said step of operating a second motor in the handle is at least partially performed while applying a longitudinally directed force to the handle.

22. A method as set forth in claim 14 wherein said step of operating a first motor in the handle is at least partially performed while manually applying a rotational force to the handle.

23. A method as set forth in claim 14 wherein said step of operating a second motor in the handle is at least partially performed while manually applying a rotational force to the handle.

* * * * *